(12) United States Patent
Gruss et al.

(10) Patent No.: US 8,058,476 B2
(45) Date of Patent: Nov. 15, 2011

(54) HCI POLYMORPHS OF 3-((2-(DIMETHYLAMINO)METHYL (CYCLOHEX-1-YL)) PHENOL

(75) Inventors: Michael Gruss, Aachen (DE); Andreas Fischer, Huertgenwald (DE); Markus Kegel, Aachen (DE); Wolfgang Hell, Aachen (DE); Markus Von Raumer, Arlesheim (CH); Joerg Berghausen, Loerrach (DE); Susan Margaret Paul, Zurich (CH)

(73) Assignee: Gruenenthal GmbH, Aachen (DE)

( * ) Notice: Subject to any disclaimer, the term of this patent is extended or adjusted under 35 U.S.C. 154(b) by 26 days.

(21) Appl. No.: 12/016,506

(22) Filed: Jan. 18, 2008

(65) Prior Publication Data

US 2008/0255242 A1    Oct. 16, 2008

Related U.S. Application Data

(63) Continuation of application No. PCT/EP2006/007163, filed on Jul. 20, 2006.

(30) Foreign Application Priority Data

Jul. 22, 2005 (DE) .......................... 10 2005 034 973
Jul. 22, 2005 (DE) .......................... 10 2005 034 974

(51) Int. Cl.
*C07C 211/00* (2006.01)
*A01N 33/02* (2006.01)
*A61K 31/135* (2006.01)

(52) U.S. Cl. .......................... 564/305; 514/646; 514/620
(58) Field of Classification Search .................. None
See application file for complete search history.

(56) References Cited

U.S. PATENT DOCUMENTS

| 5,733,936 A | * | 3/1998 | Buschmann et al. | .......... 514/646 |
| 2004/0242617 A1 | * | 12/2004 | Christoph | ................ 514/282 |
| 2005/0119349 A1 | * | 6/2005 | Buschmann et al. | .......... 514/650 |

FOREIGN PATENT DOCUMENTS

| WO | WO03/091199 | * 11/2003 |
| WO | WO 03/091199 A1 | 11/2003 |

OTHER PUBLICATIONS

International Search Report dated Oct. 31, 2006, including an English translation (Eight (8) pages).
English translation of the Written Opinion of the International Searching Authority (Form PCT/ISA/237) dated Jul. 22, 2005 (Twelve (12) pages).

* cited by examiner

*Primary Examiner* — Daniel Sullivan
*Assistant Examiner* — Clinton Brooks
(74) *Attorney, Agent, or Firm* — Crowell & Moring LLP

(57) ABSTRACT

A crystalline salt of 3-[2-(dimethylamino)methyl(cyclohex-1-yl)]phenol and hydrogen chloride, preferably in a 1:1 composition, including various crystalline forms of this salt, processes for preparing the various crystalline forms of this salt, pharmaceutical compositions containing the various crystalline forms of this salt, and the use of this salt as a pharmacologically active agent in a pharmaceutical composition to treat or inhibit pain or other disorders or disease states.

10 Claims, 10 Drawing Sheets

HCl POLYMORPHS OF 3-((2-(DIMETHYLAMINO)METHYL(CYCLOHEX-1-YL)) PHENOL

CROSS REFERENCE TO RELATED APPLICATIONS

This application is a continuation of international patent application no. PCT/EP2006/007163, filed Jul. 20, 2006 designating the United States of America and published in German on Jan. 25, 2007 as WO 2007/0009794, the entire disclosure of which is hereby incorporated herein by reference. Priority is claimed based on Federal Republic of Germany patent application nos. DE 10 2005 034 973.0 and DE 10 2005 034 974.9, both filed Jul. 22, 2005.

BACKGROUND OF THE INVENTION

The present invention relates to a crystalline salt of 3-[2-(dimethylamino)-methyl(cyclohex-1-yl)]phenol and hydrogen chloride, preferably in a composition of 1:1, to various crystalline forms of this salt and also to processes for preparation thereof, to a pharmaceutical composition, and to the use of the salt as pharmaceutical active substance in a medicament.

3-[2-(dimethylamino)methyl(cyclohex-1-yl)]phenols having analgesic activity are described in published European patent application no. EP 753,506. In the description it is mentioned that salts—such as hydrochlorides, for example—can also be prepared from the free bases of these compounds. But EP 753 506 contains no references to the fact that these hydrochlorides can be obtained in the form of a crystalline solid substance.

It has now surprisingly been found that 3-[2-(dimethylamino)methyl-(cyclohex-1-yl)]phenol forms with hydrogen chloride an addition salt in the form of a crystalline solid substance, preferably in a composition in the ratio 1:1. It has furthermore been found that 3-[2-(dimethylamino)methyl (cyclohex-1-yl)]phenol HCl in the form of crystalline solids form polymorphous forms which can each be selectively prepared and which are particularly suitable, at least partly by reason of their stability, as active substance for formulating pharmaceutical compositions. For example, the crystalline form II is suitable, by reason of its kinetic stability, as active substance for formulating pharmaceutical compositions. Moreover, the crystalline form V is suitable, by reason of its stability in the presence of water, for example in the form of atmospheric moisture, as active substance for formulating pharmaceutical compositions. Furthermore it has been found that the hydrochloride salts are distinguished by very good solubility in water. A first subject of the invention is therefore constituted by crystalline salts of hydrogen chloride with 3-[2-(dimethylamino)methyl(cyclohex-1-yl)]phenol, whereby 3-[2-(dimethylamino)methyl(cyclohex-1-yl)]phenol hydrochloride of the following formula (1) is preferred.

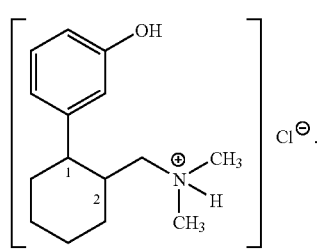

(1)

The compounds of the formula (1) contain a chiral C atom in the 1-position and 2-position of the cyclohexane ring. The compounds of the formula (1) encompass all the stereoisomers and mixtures of stereoisomers. Preferred are diastereomers or mixtures of enantiomeric diastereomers with trans configuration of the phenyl ring and of the dimethylaminomethyl group (1R,2R configuration and 1S,2S configuration, respectively), the enantiomer with the absolute configuration (1R,2R) being quite particularly preferred.

The structure of the (1R,2R) enantiomer of 3-[2-(dimethylamino)methyl-(cyclohex-1-yl)]phenol is reproduced below:

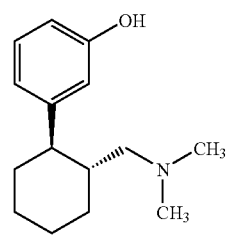

2

The invention also relates to a process for preparing 3-[2-(dimethylamino)-methyl(cyclohex-1-yl)]phenol hydrochloride of formula (1), the process comprising:
a) dissolving or suspending 3-[2-(dimethylamino)methyl(cyclohex-1-yl)]phenol in a solvent, or charging 3-[2-(dimethylamino)methyl(cyclohex-1-yl)]phenol in bulk,
b) mixing the solution, the solid substance or the suspension with a solution of hydrogen chloride, in particular hydrochloric acid, optionally cooling or heating and holding at a temperature between −80° C. and 150° C., preferably between −20° C. and 30° C., particularly preferably between −5° C. and 5° C., up until the complete formation of a solid substance, and
c) isolating the compound of the formula (1).

Alternatively, of course, 3-[2-(dimethylamino)methyl(cyclohex-1-yl)]phenol in solution, in the form of a suspension, or in bulk may also be introduced into a solution or gas containing hydrogen chloride.

The hydrochloric acid in step b) of the process stated above may, in particular, be present in the form of an aqueous solution or in the form of a solution in an organic solvent, preferably in a solvent selected from the group consisting of diethyl ether, tert.-butylmethyl ether and tetrahydrofuran.

The invention also relates to a process for preparing 3-[2-(dimethylamino)-methyl(cyclohex-1-yl)]phenol hydrochloride of formula (1), the process comprising:
a) dissolving 3-[2-(dimethylamino)methyl(cyclohex-1-yl)] phenol in a solvent, or charging 3-[2-(dimethylamino)methyl(cyclohex-1-yl)]phenol in bulk, and
b) introducing hydrogen-chloride gas into the solution or suspension, or passing hydrogen-chloride gas over the solid substance.

In the salification process according to the invention, the compounds of the formula (1) are also obtained in an amorphous form. Amorphous forms of the compounds of the formula (1) are obtainable, for example, simply by freeze drying or rapid cooling of solutions. Amorphous compounds of the formula (1) are not very stable, and in the presence of moisture tend to form hydrates. Likewise, amorphous forms of the compounds of the formula (1) in solvating solvents—such as, for example, acetone, ethanol, methanol, methyl ethyl ketone, isopropanol, n-propanol and n-octanol—are suitable for preparing the corresponding solvates. The amorphous form of the compounds of the formula (1) can likewise be used for selective preparation of crystalline forms.

It has been found that the compounds of the formula (1) in the form of crystalline solids form polymorphous forms which can be selectively prepared from 3-[2-(dimethylamino)methyl(cyclohex-1-yl)]phenol hydrochloride and which by reason of their stability are particularly suitable as active substance for formulating pharmaceutical compositions. The crystalline form II is preferably suitable, by reason of its kinetic stability, as active substance for formulating pharmaceutical compositions. Likewise the crystalline form V, by reason of its stability in the presence of water, for example in the form of atmospheric moisture, is preferably suitable as active substance for formulating pharmaceutical compositions.

It is known—inter alia, from Z. Jane Li et al. in *J. Pharm. Sci.*, 1999, Vol. 88(3), pages 337 to 346—that enantiomers yield identical X-ray diffractograms and Raman spectra, and consequently form the same polymorphous forms. Polymorphous forms of all enantiomers are consequently encompassed within the scope of this invention.

The invention further relates to a crystalline form of 3-[2-(dimethylamino)-methyl(cyclohex-1-yl)]phenol hydrochloride of the formula (1), which exhibits a characteristic X-ray diffraction pattern within the range from 2° to 35° 2θ with pronounced characteristic signals (peaks), expressed in 2-theta values:

11.2 (w), 14.1 (m), 17.1 (w), 19.5 (w), 19.8 (vs), 20.5 (w), 21.5 (m),
24.1 (m), 26.1 (s), 26.8 (w), 31.3 (m);
designated hereinafter as form I.

The invention further relates to another crystalline form I of 3-[2-(dimethylamino)methyl(cyclohex-1-yl)]phenol HCl of formula (1), which exhibits a characteristic X-ray diffraction pattern with the following pronounced reflections.

The measuring accuracy of the 2theta values lies within the range of ±0.2.

| 2Theta | Intensity (relative) |
|---|---|
| 9.09 | 1 |
| 10.22 | 1 |
| 11.22 | 24 |
| 12.21 | 4 |
| 13.03 | 2 |
| 13.47 | 3 |
| 14.12 | 43 |
| 14.90 | 15 |
| 16.69 | 3 |
| 17.16 | 24 |
| 18.05 | 10 |
| 18.89 | 14 |
| 19.53 | 26 |
| 19.78 | 100 |
| 20.22 | 12 |
| 20.48 | 28 |
| 21.46 | 43 |
| 22.24 | 11 |
| 22.50 | 21 |
| 22.71 | 19 |
| 24.12 | 34 |
| 26.09 | 73 |
| 26.81 | 43 |
| 27.68 | 22 |
| 28.26 | 25 |
| 28.51 | 14 |
| 29.96 | 14 |
| 31.28 | 46 |
| 32.58 | 8 |
| 33.03 | 6 |
| 34.52 | 15 |
| 35.44 | 28 |
| 35.67 | 15 |

-continued

| 2Theta | Intensity (relative) |
|---|---|
| 36.38 | 8 |
| 37.94 | 8 |
| 38.59 | 8 |
| 39.66 | 18 |
| 40.13 | 15 |
| 40.88 | 14 |
| 41.72 | 21 |
| 42.44 | 9 |
| 43.15 | 44 |
| 44.35 | 47 |
| 45.70 | 10 |
| 46.55 | 11 |
| 47.13 | 8 |
| 47.84 | 15 |
| 48.69 | 10 |
| 49.68 | 14 |

In this application, the abbreviations in brackets signify:
(vs)=very strong intensity,
(s)=strong intensity,
(m)=medium intensity,
(w)=weak intensity, and
(vw)=very weak intensity.

The abbreviation 'sh' in the tables of the Raman spectra signifies 'shoulder'.

The crystalline form I of 3-[2-(dimethylamino)methyl(cyclohex-1-yl)]phenol hydrochloride of the formula (1) exhibits a characteristic Raman spectrum with characteristic bands, which is described by the following wave numbers ($cm^{-1}$):

| Wave number [$cm^{-1}$] | Intensity |
|---|---|
| 82 | S |
| 107 | VS |
| 177 | W |
| 251 | M |
| 284 | VW |
| 346 | W |
| 362 | VW |
| 423 | VW |
| 434 | VW |
| 479 | VW |
| 533 | W |
| 626 | VW |
| 634 | VW |
| 754 | VW |
| 762 | W |
| 787 | VW |
| 794 | VW |
| 823 | W |
| 838 | W |
| 861 | VW |
| 884 | VW |
| 936 | VW |
| 954 | VW |
| 972 | VW |
| 1001 | VS |
| 1056 | W |
| 1070 | W |
| 1080 | VW |
| 1102 | VW |
| 1122 | VW |
| 1154 | VW |
| 1162 | VW |
| 1184 | VW |
| 1208 | VW |
| 1227 | VW |
| 1274 | W |
| 1286 | W |
| 1293 | W |
| 1306 | W |

-continued

| Wave number [cm⁻¹] | Intensity |
|---|---|
| 1316 | W |
| 1335 | VW |
| 1350 | VW |
| 1367 | VW |
| 1439 | W |
| 1449 | W |
| 1470 | W |
| 1584 | W |
| 1611 | W |
| 2633 | VW |
| 2662 | VW |
| 2714 | VW |
| 2805 | VW |
| 2856 | M |
| 2901 | M |
| 2922 | M |
| 2942 | M |
| 2957 | M |
| 2983 | W |
| 3008 | W |
| 3017 | W |
| 3025 | W |
| 3042 | W |
| 3051 | M |
| 3074 | VW |
| 3196 | VW |

In the tables, wave numbers are stated with a precision of ±4 cm⁻¹.

The invention further relates to a crystalline form I of 3-[2-(dimethylamino)methyl(cyclohex-1-yl)]phenol hydrochloride of the formula (1), which possesses a characteristic X-ray diffraction pattern as represented in FIG. 1.

The invention also relates to a crystalline form I of 3-[2-(dimethylamino)-methyl(cyclohex-1-yl)]phenol hydrochloride of the formula (1), which is characterized by a Raman spectrum as represented in FIG. 2.

The crystalline form I is thermodynamically the most stable form at low temperatures up to approximately 40° C. The crystalline form I in the presence of atmospheric moisture with a relative air humidity >50% irreversibly forms hydrates of the crystalline form V. At a relative air humidity >95%, hydrates result having a proportion of water of crystallization, relative to the total weight of the hydrate, within the range from 8% to 10%. In order to avoid the formation of hydrates, the compounds of the crystalline form I can advantageously be stored in a low-moisture environment, for example in a vessel over phosphorus pentoxide or molecular sieve. Likewise, a storage of the crystalline form I under dry protective gas (for example, nitrogen) is advisable. The melting-point amounts to approximately 150° C.

Polymorph I can be prepared in the form of solid powder having desired mean particle sizes, which, as a rule, lie within the range from 1 µm to approximately 500 µm. The compound of the formula (1) forms a further crystalline form II which is thermodynamically stable at higher temperatures and which is likewise stable under normal conditions in air and with exclusion of atmospheric moisture. The crystalline form II is also capable of being handled in such a way that it can be employed for the preparation of pharmaceutical compositions.

The invention further includes a crystalline form of 3-[2-(dimethylamino)-methyl(cyclohex-1-yl)]phenol hydrochloride of the formula (1), which exhibits a characteristic X-ray diffraction pattern within the range from 2° to 35° 2θ with pronounced characteristic lines, expressed in 2theta values:

11.1 (m), 12.9 (w), 16.1 (m), 17.1 (w), 19.1 (s), 19.6 (w), 19.9 (m), 23.2 (w), 25.8 (w), 26.1 (s), 33.6 (w);
designated hereinafter as form II.

The invention also includes a crystalline form II of 3-[2-(dimethylamino)-methyl(cyclohex-1-yl)]phenol HCl of the formula (1), which exhibits a characteristic X-ray diffraction pattern with the following pronounced reflections.

| 2Theta | Intensity (relative) |
|---|---|
| 11.06 | 56 |
| 11.55 | 12 |
| 12.97 | 27 |
| 13.70 | 18 |
| 14.10 | 6 |
| 15.03 | 9 |
| 16.15 | 55 |
| 17.07 | 25 |
| 18.48 | 4 |
| 19.10 | 100 |
| 19.56 | 25 |
| 19.90 | 36 |
| 21.13 | 11 |
| 21.95 | 9 |
| 22.21 | 4 |
| 22.66 | 15 |
| 23.26 | 26 |
| 24.64 | 15 |
| 24.95 | 4 |
| 25.43 | 7 |
| 25.82 | 22 |
| 26.12 | 82 |
| 26.71 | 4 |
| 27.02 | 19 |
| 27.66 | 8 |
| 28.44 | 6 |
| 28.72 | 5 |
| 29.07 | 3 |
| 29.65 | 7 |
| 30.34 | 6 |
| 31.44 | 5 |
| 31.95 | 6 |
| 32.42 | 14 |
| 33.62 | 15 |
| 33.99 | 7 |
| 34.64 | 7 |
| 35.21 | 5 |
| 36.17 | 10 |
| 37.39 | 2 |
| 38.30 | 3 |
| 38.96 | 3 |
| 39.24 | 4 |
| 39.62 | 10 |
| 40.35 | 2 |
| 41.26 | 4 |
| 41.82 | 3 |
| 42.38 | 3 |
| 42.89 | 5 |
| 44.16 | 3 |
| 44.76 | 4 |
| 45.35 | 11 |
| 45.85 | 4 |
| 46.18 | 2 |
| 47.09 | 3 |
| 48.45 | 3 |

A further subject of the invention is a crystalline form II of 3-[2-(dimethylamino)methyl(cyclohex-1-yl)]phenol hydrochloride of the formula (1), which exhibits a characteristic Raman spectrum with characteristic bands, which is described by the following wave numbers (cm⁻¹):

| Wave number [cm⁻¹] | Intensity |
|---|---|
| 90 | S |
| 123 | VS |

-continued

| Wave number [cm$^{-1}$] | Intensity |
|---|---|
| 171 | w |
| 230 | vw |
| 248 | m |
| 341 | w |
| 384 | vw |
| 457 | vw |
| 475 | vw |
| 505 | vw |
| 532 | w |
| 573 | vw |
| 624 | vw |
| 638 | w |
| 682 | vw |
| 706 | vw |
| 761 | w |
| 795 | w |
| 817 | vw |
| 844 | w |
| 857 | vw |
| 894 | vw |
| 936 | vw |
| 957 | vw |
| 971 | vw |
| 989 | vw |
| 997 | s |
| 1010 | vw |
| 1054 | w |
| 1075 | w |
| 1085 | vw |
| 1124 | vw |
| 1168 | vw |
| 1212 | vw |
| 1250 | vw |
| 1276 | w |
| 1294 | w |
| 1317 | vw |
| 1339 | vw |
| 1355 | vw |
| 1361 | w |
| 1391 | vw |
| 1414 | vw |
| 1441 | w |
| 1462 | w |
| 1529 | vw |
| 1586 | w |
| 1614 | w |
| 2477 | vw |
| 2519 | vw |
| 2665 | vw |
| 2734 | vw |
| 2768 | vw |
| 2814 | vw |
| 2850 | m |
| 2889 | m |
| 2920 | m |
| 2929 | s |
| 2938 | s |
| 2968 | m |
| 3019 | m |
| 3040 | w |
| 3067 | w |
| 3103 | vw |
| 3181 | vw |
| 3229 | vw |
| 3248 | vw |

The invention also relates to a crystalline form II of 3-[2-(dimethylamino)-methyl(cyclohex-1-yl)]phenol hydrochloride of the formula (1), which possesses a characteristic X-ray diffraction pattern as represented in FIG. 3.

The invention also includes a crystalline form II of 3-[2-(dimethylamino)-methyl(cyclohex-1-yl)]phenol hydrochloride of the formula (1), which is characterized by a Raman spectrum as represented in FIG. 4.

The compounds of the crystalline form II are less hygroscopic than the compounds of the crystalline forms I, III and IV, and form hydrates of the crystalline form V only at a relative air humidity >70%. For instance, after 5 hours of storage of the crystalline form II at a relative air humidity of 60% no appreciable absorption of water can be established (proportion of water <0.15 wt. %). The crystalline form II is converted only slowly, by stir-mixing in ethyl acetate at a temperature between 20° C. and 30° C., preferably at a temperature of 23° C., into the form I which is thermodynamically more stable at this temperature, so that only after 32 days has the crystalline form II been completely converted into the crystalline form I. A small proportion of the crystalline form I can be detected after three days of stir-mixing. The conversion of the crystalline form II into the crystalline form I by stir-mixing takes place only slowly also in the presence of seed crystals of the crystalline form I. The low hygroscopicity and the kinetic stability make the crystalline form II a suitable active substance in pharmaceutical formulations.

The compounds of the crystalline form II possess good chemical stability. In the presence of atmospheric moisture with a relative air humidity >70° C. they form hydrates of the crystalline form V only slowly. At a relative air humidity >95%, hydrates result having a proportion of water of crystallization, relative to the total weight of the hydrate, within the range from 8% to 10%. In order to avoid the formation of hydrates, the compounds of the crystalline form II are advantageously stored in a low-moisture environment, for example in a vessel stored over phosphorus pentoxide or molecular sieve. Likewise, a storage of the crystalline form II under dry protective gas (for example, nitrogen) is advisable.

The melting-point lies within the range between 175° C. and 178° C., and the enthalpy of fusion amounts to approximately 93.3 J/g, determined by DSC at a heating-rate of 10° C./minute. Polymorph III can be prepared in the form of solid powder having desired mean particle sizes, which, as a rule, lie within the range from 1 μm to approximately 500 μm.

The compound of the formula (1) forms a further stable crystalline form III, which is thermodynamically stable at higher temperatures, preferably at a temperature between 70° C. and 155° C., particularly preferably at a temperature between 75° C. and 151° C., and which is likewise stable under normal conditions in air and with exclusion of atmospheric moisture.

The invention also relates to a crystalline form of 3-[2-(dimethylamino)-methyl(cyclohex-1-yl)]phenol hydrochloride of the formula (1), which exhibits a characteristic X-ray diffraction pattern within the range from 2° to 35° 2θ with pronounced characteristic lines, expressed in 2theta values:

6.9 (s), 13.9 (m), 16.3 (m), 17.7 (w), 20.9 (vs), 22.1 (w), 22.5 (w), 27.8 (w);

designated hereinafter as form III.

The invention also includes a crystalline form III of 3-[2-(dimethylamino)-methyl(cyclohex-1-yl)]phenol HCl of formula I, which exhibits a characteristic X-ray diffraction pattern with the following pronounced reflections:

| 2Theta | Intensity (relative) |
|---|---|
| 6.94 | 71 |
| 8.85 | 3 |
| 10.93 | 5 |
| 11.41 | 8 |
| 12.18 | 4 |
| 13.88 | 44 |
| 16.26 | 42 |
| 16.67 | 2 |
| 17.70 | 24 |

-continued

| 2Theta | Intensity (relative) |
|---|---|
| 18.34 | 10 |
| 18.79 | 9 |
| 19.18 | 5 |
| 19.63 | 6 |
| 20.07 | 5 |
| 20.88 | 100 |
| 21.41 | 10 |
| 21.60 | 8 |
| 22.04 | 21 |
| 22.53 | 24 |
| 23.03 | 6 |
| 23.59 | 8 |
| 24.02 | 4 |
| 24.73 | 4 |
| 25.48 | 2 |
| 26.04 | 6 |
| 26.49 | 9 |
| 27.54 | 8 |
| 27.84 | 16 |
| 28.85 | 3 |
| 29.23 | 7 |
| 29.99 | 7 |
| 30.92 | 2 |
| 31.23 | 4 |
| 31.65 | 6 |
| 32.04 | 2 |
| 32.47 | 5 |
| 32.84 | 6 |
| 33.95 | 3 |
| 34.47 | 2 |
| 35.11 | 5 |
| 35.83 | 3 |
| 36.36 | 2 |
| 37.07 | 3 |
| 37.90 | 4 |
| 38.67 | 6 |
| 39.22 | 3 |
| 39.81 | 3 |
| 40.49 | 3 |
| 41.24 | 3 |
| 42.45 | 3 |
| 43.67 | 2 |
| 45.90 | 2 |
| 47.19 | 2 |
| 48.67 | 3 |

A further subject of the invention is a crystalline form III of 3-[2-(dimethylamino)methyl(cyclohex-1-yl)]phenol hydrochloride of the formula (1), which exhibits a characteristic Raman spectrum with characteristic bands, which is described by the following wave numbers ($cm^{-1}$):

| Wave number [$cm^{-1}$] | Intensity |
|---|---|
| 75.65 | S |
| 94.93 | VS |
| 194.25 | VW |
| 244.39 | M |
| 286.33 | VW |
| 338.40 | W |
| 386.13 | VW |
| 443.99 | VW |
| 456.04 | VW |
| 481.59 | VW |
| 533.66 | W |
| 573.67 | VW |
| 624.30 | VW |
| 635.87 | VW |
| 702.88 | VW |
| 755.91 | W |
| 784.36 | VW |
| 793.52 | VW |
| 797.86 | VW |
| 819.07 | VW |
| 840.29 | W |
| 848.00 | W |
| 852.34 | W |
| 869.21 | VW |
| 897.66 | VW |
| 936.71 | VW |
| 958.89 | W |
| 974.31 | VW |
| 999.87 | VS |
| 1051.45 | W |
| 1071.70 | W |
| 1103.52 | VW |
| 1124.25 | VW |
| 1147.88 | VW |
| 1159.45 | VW |
| 1167.16 | W |
| 1213.44 | VW |
| 1232.25 | VW |
| 1249.60 | VW |
| 1264.55 | VW |
| 1277.08 | VW |
| 1293.48 | W |
| 1307.94 | W |
| 1311.80 | W |
| 1335.42 | VW |
| 1367.24 | VW |
| 1399.06 | VW |
| 1431.84 | VW |
| 1444.86 | W |
| 1466.07 | W |
| 1479.09 | W |
| 1529.71 | VW |
| 1587.08 | W |
| 1605.40 | W |
| 1653.62 | VW |
| 1661.33 | VW |
| 1704.24 | VW |
| 2675.22 | W |
| 2700.29 | VW |
| 2707.04 | VW |
| 2722.95 | VW |
| 2812.14 | W |
| 2852.16 | S |
| 2858.91 | S |
| 2891.21 | M |
| 2912.91 | M |
| 2924.48 | M |
| 2939.42 | S |
| 2949.55 | M |
| 2960.63 | M |
| 3019.45 | M |
| 3048.86 | M |
| 3071.04 | W |
| 3174.69 | VW |
| 3204.10 | VW |
| 3236.41 | VW |

A further subject of the invention is a crystalline form III of 3-[2-(dimethylamino)methyl(cyclohex-1-yl)]phenol hydrochloride of the formula (1), which exhibits a characteristic X-ray diffraction pattern as shown in FIG. 5.

The invention further relates to a crystalline form III of 3-[2-(dimethylamino)methyl(cyclohex-1-yl)]phenol hydrochloride of formula (1), which is characterized by a Raman spectrum as shown in FIG. 6.

The crystalline form III in the presence of atmospheric moisture with a relative air humidity >50% irreversibly forms hydrates of the crystalline form V. At a relative air humidity >95%, hydrates result having a proportion of water of crystallization, relative to the total weight of the hydrate, within the range from 8% to 10%. In order to avoid the formation of hydrates, the compounds of the crystalline form III can advantageously be stored in a low-moisture environment, for example in a vessel over phosphorus pentoxide or a molecular sieve. Likewise, it is advisable to store the crystalline form III under dry protective gas (for example, nitrogen).

The melting-point lies within the range between 155° C. and 158° C., and the enthalpy of fusion amounts to approximately 87 J/g, determined by DSC at a heating-rate of 10° C./minute. Polymorph III can be prepared in the form of solid powder having desired mean particle sizes, which, as a rule, lie within the range from 1 μm to approximately 500 μm.

The compound of the formula (1) forms a further stable crystalline form IV which is thermodynamically stable at higher temperatures, preferably at a temperature between 70° C. and 155° C., particularly preferably at a temperature between 75° C. and 130° C., still more preferably at a temperature between 75° C. and 122° C., and which is also stable under normal conditions in air and with exclusion of atmospheric moisture.

The invention also relates to a crystalline form of 3-[2-(dimethylamino)-methyl(cyclohex-1-yl)]phenol hydrochloride of formula (1), which exhibits a characteristic X-ray diffraction pattern within the range from 20 to 35° 2θ with the following pronounced characteristic lines, expressed in 2theta values:

12.0 (m), 13.0 (m), 17.3 (m), 17.7 (m), 19.2 (s), 19.7 (m), 20.2 (m),
21.3 (m), 23.4 (m), 24.2 (m), 24.6 (m), 43.1 (vs), 44.2 (vs); designated hereinafter as form IV.

The invention also relates to a crystalline form IV of 3-[2-(dimethylamino)-methyl(cyclohex-1-yl)]phenol HCl of the formula (1), which exhibits a characteristic X-ray diffraction pattern with the following pronounced reflections:

| 2Theta | Intensity (relative) |
|---|---|
| 10.73 | 6 |
| 12.04 | 42 |
| 12.38 | 32 |
| 13.02 | 59 |
| 13.78 | 6 |
| 14.71 | 6 |
| 14.96 | 5 |
| 15.62 | 21 |
| 15.91 | 8 |
| 16.65 | 12 |
| 17.28 | 42 |
| 17.73 | 47 |
| 18.78 | 23 |
| 19.22 | 86 |
| 19.67 | 39 |
| 20.16 | 51 |
| 20.59 | 17 |
| 21.30 | 47 |
| 22.07 | 78 |
| 23.40 | 43 |
| 24.25 | 47 |
| 24.56 | 41 |
| 25.04 | 14 |
| 25.44 | 19 |
| 25.72 | 31 |
| 27.22 | 22 |
| 27.82 | 35 |
| 28.53 | 14 |
| 29.13 | 24 |
| 29.62 | 31 |
| 29.99 | 21 |
| 30.58 | 12 |
| 31.33 | 21 |
| 31.57 | 18 |
| 31.91 | 16 |
| 32.45 | 18 |
| 32.85 | 13 |
| 33.33 | 10 |
| 33.75 | 15 |
| 34.48 | 25 |
| 34.92 | 18 |
| 35.46 | 16 |
| 36.44 | 12 |
| 37.36 | 18 |
| 38.15 | 18 |
| 38.58 | 20 |
| 39.67 | 14 |
| 40.56 | 17 |
| 41.05 | 15 |
| 41.63 | 14 |
| 41.85 | 14 |
| 42.57 | 15 |
| 43.14 | 96 |
| 43.25 | 60 |
| 44.24 | 100 |
| 45.99 | 23 |
| 46.81 | 16 |
| 49.06 | 22 |

The invention also includes a crystalline form IV of 3-[2-(dimethylamino)-methyl(cyclohex-1-yl)]phenol hydrochloride of the formula (1), which exhibits a characteristic Raman spectrum with characteristic bands described by the following wave numbers ($cm^{-1}$):

| Wave number [$cm^{-1}$] | Intensity |
|---|---|
| 85 | s |
| 115 | s |
| 123 | s |
| 190 | vw |
| 243 | m |
| 337 | w |
| 386 | vw |
| 448 | vw |
| 476 | vw |
| 502 | vw |
| 534 | w |
| 574 | vw |
| 625 | w |
| 637 | vw |
| 709 | vw |
| 724 | vw |
| 748 | w |
| 761 | w |
| 794 | vw |
| 819 | vw |
| 833 | w |
| 844 | w |
| 858 | vw |
| 891 | vw |
| 913 | vw |
| 936 | vw |
| 957 | vw |
| 970 | vw |
| 988 | vw |
| 999 | vs |
| 1052 | w |
| 1071 | vw |
| 1083 | vw |
| 1104 | vw |
| 1123 | vw |
| 1160 | w |
| 1211 | vw |
| 1251 | vw |
| 1278 | w |
| 1293 | w |
| 1321 | w |
| 1337 | vw |
| 1366 | w |
| 1401 | vw |

| Wave number [cm⁻¹] | Intensity |
|---|---|
| 1444 | W |
| 1463 | W |
| 1476 | VW |
| 1585 | W |
| 1614 | W |
| 2665 | VW |
| 2684 | VW |
| 2697 | VW |
| 2701 | VW |
| 2817 | W |
| 2853 | M |
| 2897 | M |
| 2914 | M |
| 2925 | M |
| 2938 | S |
| 2964 | M |
| 3017 | W |
| 3028 | W |
| 3043 | M |
| 3074 | VW |
| 3083 | VW |

The invention also relates to a crystalline form IV of 3-[2-(dimethylamino)-methyl(cyclohex-1-yl)]phenol hydrochloride of the formula (1), which exhibits a characteristic X-ray diffraction pattern as shown in FIG. 7.

The invention additionally includes a crystalline form IV of 3-[2-(dimethylamino)methyl(cyclohex-1-yl)]phenol hydrochloride of formula (1), which is characterized by a Raman spectrum as shown in FIG. 8.

In the presence of atmospheric moisture at a relative air humidity >50%, the crystalline form IV irreversibly forms hydrates of the crystalline form V. At a relative air humidity >95%, hydrates result having a proportion of water of crystallization, relative to the total weight of the hydrate, within the range from 8% to 10%. In order to avoid the formation of hydrates, the compounds of the crystalline form IV can advantageously be stored in a low-moisture environment, for example in a vessel over phosphorus pentoxide or over a molecular sieve. Likewise, it is advisable to store the crystalline form IV under dry protective gas (for example, nitrogen).

The melting-point lies within the range between 166° C. and 172° C., and the enthalpy of fusion amounts to approximately 78 J/g, determined by DSC at a heating-rate of 10° C./minute. Polymorph IV can be prepared in the form of solid powder having desired mean particle sizes, which, as a rule, lie within the range from 1 μm to approximately 500 μm.

The compound of the formula (1) furthermore forms stable hydrates of the crystalline form V, which are stable in air under normal conditions.

The hydrates of the crystalline form V preferably exhibit a content of water of crystallization within the range from 1% to 10%, particularly preferably within the range from 5% to 9%, quite particularly preferably within the range from 6% to 8.5%, still more preferably within the range from 7% to 8%, relative to the weight of the hydrate.

The invention also relates to a crystalline form of 3-[2-(dimethylamino)-methyl(cyclohex-1-yl)]phenol hydrochloride of the formula (1), which exhibits a characteristic X-ray diffraction pattern within the range from 20 to 35° 2θ with pronounced characteristic lines, expressed in 2theta values:

11.4 (m), 12.1 (m), 16.7 (w), 19.2 (m), 19.4 (w), 20.1 (m), 21.1 (m),
22.4 (vs), 24.0 (m), 31.3 (w);
designated in the following as form V.

The invention further relates to a crystalline form V of 3-[2-(dimethylamino)methyl(cyclohex-1-yl)]phenol HCl of formula (1), which exhibits a characteristic X-ray diffraction pattern with the following pronounced reflections.

| 2Theta | Intensity (relative) |
|---|---|
| 9.06 | 6 |
| 11.47 | 60 |
| 12.15 | 36 |
| 13.43 | 9 |
| 14.32 | 11 |
| 14.89 | 6 |
| 16.72 | 17 |
| 17.42 | 4 |
| 18.12 | 5 |
| 18.82 | 6 |
| 19.23 | 46 |
| 19.44 | 31 |
| 20.07 | 50 |
| 20.68 | 8 |
| 21.09 | 50 |
| 21.88 | 8 |
| 22.42 | 100 |
| 23.00 | 5 |
| 23.53 | 6 |
| 24.04 | 46 |
| 24.37 | 33 |
| 24.54 | 26 |
| 24.58 | 27 |
| 25.05 | 7 |
| 25.89 | 29 |
| 26.52 | 7 |
| 26.99 | 6 |
| 27.32 | 12 |
| 27.91 | 13 |
| 28.65 | 10 |
| 30.11 | 13 |
| 30.93 | 17 |
| 31.29 | 20 |
| 32.43 | 17 |
| 32.96 | 11 |
| 33.74 | 5 |
| 34.11 | 6 |
| 34.46 | 7 |
| 34.84 | 9 |
| 35.89 | 7 |
| 36.31 | 6 |
| 36.88 | 7 |
| 37.38 | 12 |
| 37.71 | 8 |
| 38.06 | 5 |
| 38.99 | 7 |
| 40.01 | 7 |
| 40.72 | 5 |
| 41.70 | 4 |
| 42.35 | 5 |
| 42.94 | 8 |
| 43.86 | 5 |
| 44.15 | 5 |
| 44.70 | 4 |
| 45.07 | 6 |
| 45.65 | 6 |
| 46.24 | 5 |
| 47.31 | 6 |
| 48.23 | 4 |
| 49.12 | 4 |

The invention also includes a crystalline form V of 3-[2-(dimethylamino)-methyl(cyclohex-1-yl)]phenol hydrochloride of formula (1), which exhibits a characteristic Raman spectrum with characteristic bands described by the following wave numbers (cm⁻¹):

| Wave number [cm⁻¹] | Intensity |
| --- | --- |
| 96.38 | VS |
| 252.59 | W |
| 270.91 | W |
| 337.44 | W |
| 371.67 | VW |
| 448.81 | VW |
| 469.06 | VW |
| 507.14 | VW |
| 535.11 | W |
| 572.23 | VW |
| 624.30 | VW |
| 704.81 | VW |
| 751.58 | W |
| 794.48 | VW |
| 817.14 | VW |
| 837.39 | W |
| 857.16 | VW |
| 886.09 | VW |
| 915.01 | VW |
| 935.26 | VW |
| 952.62 | VW |
| 999.38 | S |
| 1053.38 | W |
| 1100.15 | VW |
| 1120.40 | VW |
| 1159.45 | VW |
| 1211.03 | VW |
| 1251.05 | VW |
| 1271.78 | VW |
| 1294.44 | W |
| 1308.42 | VW |
| 1336.87 | VW |
| 1355.19 | VW |
| 1368.69 | W |
| 1405.81 | VW |
| 1440.52 | W |
| 1459.81 | W |
| 1502.71 | VW |
| 1600.58 | W |
| 2667.03 | VW |
| 2702.70 | VW |
| 2728.74 | VW |
| 2811.66 | VW |
| 2855.05 | M |
| 2895.55 | M |
| 2934.60 | M |
| 2966.42 | M |
| 3032.47 | W |

The invention also relates to a crystalline form V of 3-[2-(dimethylamino)-methyl(cyclohex-1-yl)]phenol hydrochloride of the formula (1), which exhibits a characteristic X-ray diffraction pattern as shown in FIG. 9.

The invention additionally relates to a crystalline form V of 3-[2-(dimethylamino)methyl(cyclohex-1-yl)]phenol hydrochloride of the formula (1), which is characterized by a Raman spectrum as represented in FIG. 10.

The crystalline form V is stable at ambient temperature in air and is therefore particularly suitable as an active substance in pharmaceutical formulations.

The crystalline form V can be dehydrated only with difficulty. The use of vacuum and/or of hygroscopic reagents—such as phosphorus pentoxide, for example—results only in an incomplete release of water from the crystalline form V. In the presence of water—which may be present, for example, in the form of water vapor or atmospheric moisture—the partially dehydrated compound of the crystalline form V quickly absorbs said water again. The compounds of the crystalline form V do not change under elevated pressure—for example, at a pressure of 8000 bar for a period of 60 minutes—or in the course of grinding, and no conversion into the crystalline forms I, II, III or IV is observed under the influence of elevated pressure.

The melting-point of the compounds of the crystalline form V lies within the temperature range from 105° C. to 115° C., and the enthalpy of fusion determined by DSC at a heating-rate of 10° C./minute amounts to approximately 77 J/g.

The compound of the formula (1) forms stable solvates in solvating solvents such as, for example, ethanol, methanol, methyl ethyl ketone, isopropanol, n-propanol, n-octanol and acetone. The solvates are isomorphous to one another and likewise to the hydrate having the crystalline form V. The solvent cannot be removed, or cannot be completely removed, by vacuum.

The replacement of ethanol in an appropriate solvate of compounds of the formula (1) is possible by storage at elevated air humidity, for example by storage in the presence of a supersaturated aqueous solution of magnesium nitrate or in the presence of a supersaturated aqueous solution of sodium chloride for a period of at least two months, preferably for a period of at least four months.

The polymorphous forms I, II, III, IV and V can each be converted into other crystalline forms. For example, the polymorphous forms II, III and IV can be converted into the polymorphous form I; the polymorphous forms III and IV can be converted into the polymorphous form II; the polymorphous forms III can be converted into the polymorphous form IV, and the polymorphous forms I and II can be converted into the polymorphous forms III or IV. A further subject of the invention is therefore also constituted by mixtures of the crystalline forms I, II, III, IV and V in, as such, arbitrary mixing ratios.

The crystal lattices of forms I, II, III, IV and V are clearly different from one another, so that the Raman spectra and X-ray diffraction patterns exhibit great differences. For instance, form I exhibits a peak with strong intensity within the range of 19°2θ, form III exhibits peaks with strong intensity within the ranges of 7°, 14° and 21° 2θ, and form V exhibits peaks with strong intensity within the ranges of 12° and 22° 2θ.

The polymorphous forms I, II, III and IV can be prepared by crystallization procedures known as such from the salt 3-[2-(dimethylamino)methyl(cyclohex-1-yl)]phenol hydrochloride, for example by stirring of suspensions (adjustment of phase equilibria), precipitation, recrystallization, evaporation of solvents or crystallization from the melt. Diluted, saturated or supersaturated solutions may be used, with or without seeding with a crystal nucleator. The temperatures for forming solutions may amount to up to 100° C. The crystallization can be initiated by cooling to approximately −100° C. to 30° C., and preferably −30° C. to 20° C., whereby cooling may take place continuously or in stepwise manner. For the purpose of preparing solutions or suspensions, use may be made of amorphous or crystalline starting materials, in order to achieve high concentrations in solutions and to obtain other crystalline forms.

The invention therefore also relates to a process for preparing the crystalline form I of 3-[2 (dimethylamino)methyl (cyclohex-1-yl)]phenol hydrochloride, wherein:
a) 3-[2-(dimethylamino)methyl(cyclohex-1-yl)]phenol hydrochloride in the crystalline form III and 3-[2-(dimethylamino)methyl(cyclohex-1-yl)]phenol hydrochloride in the crystalline form IV or 3-[2-(dimethylamino)methyl-(cyclohex-1-yl)phenol hydrochloride in the crystalline form V are stirred in a solvent, preferably in a quantitative ratio between 1:100 and 100:1, particularly preferably in a quantitative ratio between 1:10 and 10:1, quite particularly preferably in a quantitative ratio between 1:5 and 5:1, up until the complete formation of the crystalline form I, or b) 3-[2-(dimethylamino)methyl(cyclohex-1-yl)]phenol hydrochloride in the crystalline form II and 3-[2-(dimethylamino)methyl(cyclohex-1-yl)]phenol hydrochloride in the crystalline form I are stirred in a solvent, preferably in a quantitative ratio between 100:1 and 8:1, particularly preferably in a quantitative ratio between 11:1 and 9:1, up until the complete formation of the crystalline form I, whereby the temperature in processes a) and b) is at most 40° C., preferably at most 30° C., particularly preferably at most 25° C.

Processes a) and b) can be carried out in the presence of air or in the presence of inert gases such as, for example, nitrogen and noble gases. It is preferred to work in an air environment for economic reasons. The relative humidity of the gases preferably is <50%, particularly preferably <20%, especially preferably <5%.

The duration of processes a) and b) depends substantially on the size of the crystals and on the concentration of 3-[2-(dimethylamino)methyl(cyclohex-1-yl)]phenol hydrochloride, and may preferably amount to from 1 hour to 250 hours, particularly preferably 3 hours to 72 hours, and especially preferably 5 hours to 25 hours. The concentration of 3-[2-(dimethylamino)methyl(cyclohex-1-yl)]phenol hydrochloride preferably amounts to 0.5% to 50%, particularly preferably 2% to 30%, quite particularly preferably 5% to 20%, still more preferably 5% to 8%, in each instance relative to the weight of the solvent.

After isolation, the crystalline residue can be dried in conventional manner, whereby temperatures above 40° C. are advantageously avoided.

Processes a) and b) are preferably carried out in non-solvating solvents. Particularly preferred are solvents selected from the group consisting of aliphatic, cycloaliphatic and aromatic hydrocarbons (hexane, heptane, petroleum ether, cyclohexane, methyl cyclohexane, benzene, toluene, xylene), aliphatic halogenated hydrocarbons (dichloromethane, chloroform, dichloroethane and tetrachloroethane), nitriles (acetonitrile, propionitrile, benzonitrile), ethers (diethyl ether, dibutyl ether, tert.-butylmethyl ether, ethylene glycol dimethyl ether, ethylene glycol diethyl ether, diethylene glycol dimethyl ether, tetrahydrofuran, methyl tetrahydrofuran, dioxan), long-chain alcohols (butanol, tert.-butanol, pentanol, octanol, decanol) and carboxylic-acid esters and lactones propyl acetate, ethyl acetate or methyl acetate, valerolactone). The solvent ethyl acetate is especially preferred.

The solvents can be used individually or in a mixture of at least two solvents. It is preferred to use physiologically harmless solvents that are known to persons skilled in the art. After isolation, the solvent or solvent mixture that has been used can be removed in conventional manner by known drying processes.

The invention also relates to a crystalline form I of 3-[2-(dimethylamino)-methyl(cyclohex-1-yl)]phenol hydrochloride of the formula (1), obtainable by one of the processes described above.

The invention additionally includes a process for preparing the crystalline form II of 3-[2-(dimethylamino)methyl(cyclohex-1-yl)]phenol hydrochloride, wherein a) 3-[2-(dimethylamino)methyl(cyclohex-1-yl)]phenol hydrochloride in the crystalline form IV or a mixture of 3-[2-(dimethylamino)methyl(cyclohex-1-yl)]phenol hydrochloride in the crystalline form III and 3-[2-(dimethylamino)-methyl(cyclohex-1-yl)]phenol hydrochloride in the crystalline form V is heat-treated at a temperature between 150° C. and 160° C., preferably at a temperature between 154° C. and 158° C., up until the complete formation of the crystalline form II, or b) 3-[2-(dimethylamino)methyl(cyclohex-1-yl)]phenol hydrochloride in the crystalline form II and 3-[2-(dimethylamino)methyl(cyclohex-1-yl)]phenol hydrochloride in the crystalline form III or 3-[2-(dimethylamino)methyl-(cyclohex-1-yl)]phenol hydrochloride in the crystalline form IV is stirred in a solvent, preferably in a quantitative ratio between 1:100 and 1:8, particularly preferably in a quantitative ratio between 1:11 and 1:9, up until the complete formation of the crystalline form II, or c) a suspension of the amorphous form of 3-[2-(dimethylamino)methyl(cyclohex-1-yl)]phenol hydrochloride in a solvent, preferably a solvent that does not form solvates, as a carrier is stirred at a temperature between 30° C. and 50° C., preferably at a temperature between 35° C. and 45° C., particularly preferably at a temperature of 40° C., until the complete formation of the crystalline form II occurs; or d) 3-[2-(dimethylamino)methyl(cyclohex-1-yl)]phenol hydrochloride in the crystalline form III and 3-[2-(dimethylamino)methyl(cyclohex-1-yl)]phenol hydrochloride in the crystalline form IV are stirred in a solvent, preferably in a quantitative ratio between 1:100 and 100:1, particularly preferably in a quantitative ratio between 1:10 and 10:1, especially preferably in a quantitative ratio between 1:5 and 5:1, until the complete formation of the crystalline form II occurs;

whereby the temperature in processes b) and d) is at most 60° C., preferably at most 40° C., particularly preferably at most 30° C., especially preferably at most 25° C.

Processes b), c) and d) can be carried out in the presence of air or in the presence of inert gases such as, for example, nitrogen and noble gases. It is preferred to work in an air environment for economic reasons. The relative humidity of the gases preferably is <50%, particularly preferably <20%, especially preferably <5%.

The duration of processes b) and d) depends substantially on the size of the crystals and on the concentration of 3-[2-(dimethylamino)methyl(cyclohex-1-yl)]phenol hydrochloride, and may preferably amount to from 1 hour to 250 hours, particularly preferably 3 hours to 72 hours, especially preferably 5 hours to 25 hours. The duration of process c) preferably amounts to at least 300 hours, particularly preferably at least 350 hours, especially preferably at least 400 hours. The concentration of 3-[2-(dimethylamino)methyl(cyclohex-1-yl)]phenol hydro-chloride in processes b), c) and d) preferably is 0.5% to 50%, particularly preferably 2% to 30%, quite particularly preferably 5% to 20%, still more preferably 5% to 8%, in each instance relative to the weight of the solvent.

Processes b), c) and d) are preferably carried out in non-solvating solvents. Particularly preferred are solvents selected from the group consisting of aliphatic, cycloaliphatic and aromatic hydrocarbons (hexane, heptane, petroleum ether, cyclohexane, methyl cyclohexane, benzene, toluene, xylene), aliphatic halogenated hydrocarbons (dichloromethane, chloroform, dichloroethane and tetrachloroethane), nitriles (acetonitrile, propionitrile, benzonitrile), ethers (diethyl ether, dibutyl ether, tert.-butyl methyl ether, ethylene glycol dimethyl ether, ethylene glycol diethyl ether, diethylene glycol dimethyl ether, tetrahydrofuran, methyl tetrahydrofuran, dioxan), long-chain alcohols (butanol, tert.-butanol, pentanol, octanol, decanol) and carboxylic-acid esters and lactones (propyl acetate, ethyl acetate or methyl acetate, valerolactone). The solvent ethyl acetate is especially preferred.

The solvents can be used individually or in a mixture of at least two solvents. It is advantageous to use physiologically harmless solvents that are known to persons skilled in the art.

After isolation, the solvent and/or solvent mixture that has been used can be removed in conventional manner by known drying processes.

The invention also relates to a crystalline form II of 3-[2-(dimethylamino)-methyl(cyclohex-1-yl)]phenol hydrochloride of formula (1), obtainable by one of the processes described above.

The invention likewise relates to a process for preparing the crystalline form III of 3-[2-(dimethylamino)methyl(cyclohex-1-yl)]phenol hydrochloride, wherein a) 3-[2-(dimethylamino)methyl(cyclohex-1-yl)]phenol hydrochloride in the form of an ethanol solvate or acetone solvate is dissolved in a solvent and stirred and subsequently precipitated, or b) a suspension of the amorphous form of 3-[2-(dimethylamino)methyl(cyclohex-1-yl)]phenol hydrochloride in a solvent, preferably in a solvent that does not form solvates, as a carrier, is stirred at a temperature between 30° C. and 80° C., preferably at a temperature between 35° C. and 50° C., particularly preferably at a temperature of 40° C., until complete formation of the crystalline form III occurs.

In process step a) the crystalline forms I, II, IV, the amorphous form of 3-[2-(dimethylamino)methyl(cyclohex-1-yl)]phenol hydrochloride or corresponding mixtures can be used for preparing solutions. The concentration of 3-[2-(dimethylamino)methyl(cyclohex-1-yl)]phenol hydrochloride in the solution depends on the chosen temperature and on the solvent. The dissolved quantity may preferably amount to from 0.5% to 50%, particularly preferably from 2% to 30%, quite particularly preferably 3% to 25%, and still more preferably 5% to 20%, relative to the solvent. The dissolution temperature may be up to 70° C. and preferably up to 60° C. Ethyl acetate is preferably used as solvent for preparing solutions.

Precipitation can be effected by cooling, partial or complete removal of the solvent, addition of a solvent in which 3-[2-(dimethylamino)methyl(cyclohex-1-yl)]phenol hydrochloride exhibits only a low solubility—such as, for example, heptane, tert.-butylmethyl ether or ethyl acetate and corresponding mixtures—or by a combination of these measures. 'Cooling' may signify slow cooling or chilling to temperatures down to −20° C. and preferably to 0° C. The solvent can be removed by heating, in a stream of gas, applying a vacuum, or a combination of these measures. In process stage a), heating for the purpose of removing solvent implies a temperature of at most 40° C., and preferably of at most 30° C.

Process b) can be carried out in the presence of air or in the presence of inert gases such as, for example, nitrogen and noble gases. It is preferred to work in an air environment for economic reasons. The relative humidity of the gases preferably is <50%, particularly preferably <40%, especially preferably <20%.

The duration of process b) depends substantially on the size of the crystals and on the concentration of 3-[2-(dimethylamino)methyl(cyclohex-1-yl)]phenol hydrochloride, and may preferably amount to from 1 hour to 350 hours, particularly preferably 10 hours to 300 hours, especially preferably 20 hours to 300 hours. The concentration of 3-[2-(dimethylamino)methyl(cyclohex-1-yl)]-phenol hydrochloride in process b) preferably amounts to 0.5% to 50%, particularly preferably 2% to 30%, quite particularly preferably 5% to 20%, still more preferably 5% to 15%, in each instance relative to the weight of the solvent. After isolation, the crystalline residue can be dried in conventional manner, whereby temperatures above 40° C. are advantageously avoided.

Process b) is preferably carried out in non-solvating solvents. Particularly preferred are solvents selected from the group consisting of aliphatic, cycloaliphatic and aromatic hydrocarbons (hexane, heptane, petroleum ether, cyclohexane, methyl cyclohexane, benzene, toluene, xylene), aliphatic halogenated hydrocarbons (dichloromethane, chloroform, dichloroethane and tetrachloroethane), nitriles (acetonitrile, propionitrile, benzonitrile), ethers (diethyl ether, dibutyl ether, tert.-butylmethyl ether, ethylene glycol dimethyl ether, ethylene glycol diethyl ether, diethylene glycol dimethyl ether, tetrahydrofuran, methyl tetrahydrofuran, dioxan), long-chain alcohols (butanol, tert.-butanol, pentanol, octanol, decanol) and carboxylic-acid esters and lactones (propyl acetate, ethyl acetate or methyl acetate, valerolactone). The solvents heptane, tert.-butylmethyl ether and ethyl acetate are especially preferred.

The invention also relates to a crystalline form III of 3-[2-(dimethylamino)-methyl(cyclohex-1-yl)]phenol hydrochloride of the formula (1), obtainable by one of the processes described above.

The invention likewise relates to a process for preparing the crystalline form IV of 3-[2-(dimethylamino)methyl(cyclohex-1-yl)]phenol hydrochloride, wherein a) 3-[2-(dimethylamino)methyl(cyclohex-1-yl)]phenol hydrochloride in the crystalline form III is heat-treated at a temperature between 150° C. and 160° C., preferably at a temperature between 154° C. and 158° C., until complete formation of the crystalline form IV occurs, or b) a suspension of the amorphous form of 3-[2-(dimethylamino)methyl(cyclohex-1-yl)]phenol hydrochloride in a solvent, preferably in a solvent that does not form solvates, as a carrier, is stirred at a temperature between 40° C. and 120° C., preferably at a temperature between 40° C. and 100° C., particularly preferably at a temperature between 40° C. and 80° C., until complete formation of the crystalline form IV occurs; or c) 3-[2-(dimethylamino)methyl(cyclohex-1-yl)]phenol hydrochloride in the crystalline form IV and 3-[2-(dimethylamino)methyl(cyclohex-1-yl)]phenol hydrochloride in the crystalline form III are stirred in a solvent, preferably in a quantitative ratio between 1:100 and 1:8, particularly preferably in a quantitative ratio between 1:11 and 1:9, until complete formation of the crystalline form IV occurs; whereby the temperature in process c) is at most 40° C., preferably at most 30° C., particularly preferably at most 25° C.

Processes b) and c) can be carried out in the presence of air or in the presence of inert gases such as, for example, nitrogen and noble gases. It is preferred to work in an air environment for economic reasons. The relative humidity of the gases preferably is <50%, particularly preferably <40%, especially preferably <20%.

The duration of processes b) and c) depends substantially on the size of the crystals and on the concentration of 3-[2-(dimethylamino)methyl(cyclohex-1-yl)]phenol hydrochloride, and may preferably amount to from 1 hour to 250 hours, particularly preferably 10 hours to 200 hours, especially preferably 30 hours to 150 hours. The concentration of 3-[2-(dimethylamino)methyl(cyclohex-1-yl)]-phenol hydrochloride preferably amounts to 0.5% to 50%, particularly preferably 0.5% to 20%, quite particularly preferably 0.5% to 10%, still more preferably 1% to 8%, in each instance relative to the weight of the solvent. After isolation, the crystalline residue can be dried in conventional manner, whereby temperatures above 40° C. are advantageously avoided.

Processes b) and c) are preferably implemented in non-solvating solvents. Particularly preferred are solvents selected from the group consisting of aliphatic, cycloaliphatic and aromatic hydrocarbons (hexane, heptane, petroleum ether, cyclohexane, methyl cyclohexane, benzene, toluene, xylene), aliphatic halogenated hydrocarbons (dichloromethane, chloroform, dichloroethane and tetrachloroethane), nitriles (acetonitrile, propionitrile, benzonitrile), ethers (diethyl ether, dibutyl ether, tert.-butylmethyl ether, ethylene glycol dimethyl ether, ethylene glycol diethyl ether, diethylene glycol dimethyl ether, tetrahydrofuran, methyl tetrahydrofuran, dioxan), long-chain alcohols (butanol, tert.-butanol, pentanol, octanol, decanol) and carboxylic-acid esters and lactones (propyl acetate, ethyl acetate or methyl acetate, valerolactone). The solvent tert.-butylmethyl ether is especially preferred.

The solvents can be used individually or in a mixture of at least two solvents. It is advantageous to use physiologically harmless solvents that are known to persons skilled in the art. After isolation, the solvent and/or solvent mixture that has been used can be removed in conventional manner by known drying processes.

The invention further relates to a crystalline form IV of 3-[2-(dimethyl-amino)methyl(cyclohex-1-yl)]phenol hydrochloride of formula (1), obtainable by one of the processes described above.

The invention likewise includes a process for preparing the crystalline form V of 3-[2-(dimethylamino)methyl(cyclohex-1-yl)]phenol hydrochloride, wherein
a)  3-[2-(dimethylamino)methyl(cyclohex-1-yl)]phenol hydrochloride in the crystalline form I, II, III or IV is left to stand in air or is treated with water vapor, or
b) a suspension of the amorphous form of 3-[2-(dimethylamino)methyl(cyclohex-1-yl)]phenol hydrochloride in a mixture of water and optionally at least one solvent as a carrier, is stirred at a temperature between 20° C. and 60° C., preferably at a temperature between 20° C. and 30° C., and subsequently the remaining water or solvent is removed.

The invention also includes a crystalline form V of 3-[2-(dimethylamino)-methyl(cyclohex-1-yl)]phenol hydrochloride of formula (1), obtainable by one of the processes described above.

Due to its favorable overall profile of properties, 3-[2-(dimethylamino)-methyl(cyclohex-1-yl)]phenol hydrochloride, in particular 3-[2-(dimethylamino)-methyl(cyclohex-1-yl)]phenol hydrochloride in the crystalline forms II and V, is outstandingly suitable as an active substance for pharmaceutical compositions and quite particularly suitable for pain-relieving medicaments. Accordingly, the invention also includes the use of 3-[2-(dimethylamino)methyl(cyclohex-1-yl)]phenol hydrochloride of formula (1) as an active substance in a pharmaceutical composition or medicament, preferably as an active substance in an analgesic.

Preferred here also, as in the entire application, are diastereomers or mixtures of enantiomeric diastereomers with trans configuration of the phenyl ring and of the dimethylaminomethyl group (1R,2R configuration and 1S,2S configuration, respectively), the enantiomer with the absolute configuration (1R,2R) being quite particularly preferred.

The invention also includes a pharmaceutical composition containing a pharmacologically effective amount of 3-[2-(dimethylamino)methyl(cyclohex-1-yl)]phenol hydrochloride of formula (1) and at least one pharmaceutical carrier or diluent.

In the composition the compound of the formula (1) may be present as crystalline form I, II, III, IV, V or as a mixture of forms I, II, III, IV and V. The crystalline form II and/or I and/or V is preferably included. The crystalline form II and/or V is particularly preferably included.

The conversion of the compounds of the crystalline form II into the crystalline form I in pharmaceutical compositions can be prevented through the use of pharmaceutically acceptable ingredients and components or through the use of suitable formulation auxiliaries known to a person skilled in the art.

The quantity of the compounds of the formula (1) depends substantially on the type of formulation and on the desired dosage during the period of administration. The quantity of the respective compounds of the formula (1) to be administered to the patient may vary and is, for example, dependent on the weight or age of the patient and also on the manner of administration, on the indication and on the degree of severity of the illness. Preferably 0.005 mg/kg to 5000 mg/kg, particularly preferably 0.05 mg/kg to 500 mg/kg, quite particularly preferably 0.5 mg/kg to 100 mg/kg, still more preferably 2 mg/kg to 20 mg/kg of body weight of the patient of at least one such compound are administered.

Oral formulations may be solid formulations, for example tablets, capsules, pills and pastilles, but oral formulations may also be liquid formulations, for example solutions, suspensions, syrups or elixirs. Liquid and solid formulations also encompass the incorporation of the compounds of the formula (1) into solid or liquid foodstuffs. Furthermore, liquids also encompass solutions for parenteral applications, such as, for example, solutions for infusion or injection.

The compounds of the formula (1) and the crystalline forms can be used directly as powders (micronized particles), granulates, suspensions or solutions, or they may be mixed with other pharmaceutically acceptable ingredients and components and then pulverized, in order then to fill the powders into capsules consisting of hard or soft gelatin, to press tablets, pills or pastilles, or in order to suspend or dissolve the powders in a carrier for the purpose of preparing suspensions, syrups or elixirs. Tablets, pills or pastilles can be provided with a coating after pressing.

Pharmaceutically acceptable ingredients and components for the various types of formulation are known as such. It may, for example, be a question of binding agents such as synthetic or natural polymers, medicinal carriers, lubricating agents, surfactants, sweetening agents and flavoring agents, coating agents, preserving agents, dyestuffs, thickening agents, ancillary agents, antimicrobial agents and carriers for the various types of formulation.

Examples of suitable binding agents include gum arabic, gum tragacanth, acacia gum and biodegradable polymers such as homopolyesters or copolyesters of dicarboxylic acids, alkylene diols, polyalkylene glycols and/or aliphatic hydroxycarboxylic acids; homopolyamides or copolyamides of dicarboxylic acids, alkylenediamines and/or aliphatic aminocarboxylic acids; corresponding polyester-polyamide copolymers, polyanhydrides, polyorthoesters, polyphosphazenes and polycarbonates. The biodegradable polymers may be linear, branched or crosslinked. Specific examples are polyglycolic acid, polylactic acid and poly-d,l-lactic/glycolic acid. Other examples of polymers are water-soluble polymers such as, for example, polyoxaalkylenes (polyoxyethylene, polyoxypropylene and mixed polymers thereof), polyacrylamides and hydroxyl-alkylated polyacrylamides, polymaleic acid and esters or amides thereof, polyacrylic acid and esters or amides thereof, polyvinyl alcohol and esters or ethers thereof, polyvinyl imidazole, polyvinyl pyrrolidone and natural polymers, such as chitosan, for example.

Examples of medicinal carriers include phosphates, such as dicalcium phosphate.

Examples of suitable lubricating agents include natural or synthetic oils, fats, waxes or fatty-acid salts such as magnesium stearate.

Surfactants (surface-active agents) may be anionic, cationic, amphoteric or neutral. Examples of useful surfactants include lecithin, phospholipids, octyl sulfate, decyl sulfate, dodecyl sulfate, tetradecyl sulfate, hexadecyl sulfate and octadecyl sulfate, sodium oleate or sodium caprate, 1-acyl-aminoethane-2-sulfonic acids such as 1-octanoylaminoethane-2-sulfonic acid, 1-decanoylaminoethane-2-sulfonic acid, 1-dodecanoylaminoethane-2-sulfonic acid, 1-tetradecanoylamino-ethane-2-sulfonic acid, 1-hexadecanoylaminoethane-2-sulfonic acid and 1-octadecanoylaminoethane-2-sulfonic acid, bile acids, salts and derivatives thereof, such as, for example, cholic acid, deoxycholic acid, taurocholic acid, taurodeoxycholic acid and sodium glycocholates, sodium caprate, sodium laurate, sodium oleate, sodium lauryl sulfate, sodium cetyl sulfate, sulfated castor oil, sodium dioctyl sulfosuccinate, cocamidopropyl betaine and lauryl betaine, fatty alcohols, cholesterols, glycerin monostearate or distearate, glycerin monooleate or dioleate, glycerin monopalmitate or dipalmitate and polyoxyethylene stearate.

Examples of suitable sweetening agents include sucrose, fructose, lactose and aspartame.

Examples of useful flavoring agents include peppermint, oil of wintergreen or fruit flavor such as cherry or orange flavor.

Examples of suitable coating agents include gelatins, waxes, shellac, sugars and biodegradable polymers.

Examples of preservation agents include methylparaben or propylparaben, sorbic acid, chlorobutanol and phenol.

Examples of ancillary agents include aromatic principles.

Examples of suitable thickening agents include synthetic polymers, fatty acids, fatty-acid salts, fatty-acid esters and fatty alcohols.

Examples of suitable liquid carriers include water, alcohols (ethanol, glycerol, propylene glycol, liquid polyethylene glycols), polytriazines and oils. Examples of solid carriers are talc, aluminas, microcrystalline cellulose, silicon dioxide, aluminium oxide and similar solid substances.

The composition according to the invention may also contain isotonic agents such as, for example, sugars, physiological buffers and sodium chloride.

The composition according to the invention may also be formulated as an effervescent tablet or effervescent powder which decomposes in an aqueous environment, thereby formulating solutions or suspensions for drinking.

A syrup or a elixir may contain the compound of the formula (1), a sugar such as sucrose or fructose by way of sweetening agent, a preserving agent (such as methylparaben), a dyestuff and a flavoring agent (such as flavoring substances).

The composition according to the invention may also be a formulation with delayed and/or controlled release of the active substance upon contact with body fluids of the gastrointestinal tract, in order to achieve a substantially constant and effective level of the active substance in the blood plasma. For this purpose the compounds of the formula (1) can be embedded in a polymer matrix of a biodegradable polymer, of a water-soluble polymer or of both types of polymers, optionally together with a suitable surfactant. In this context, 'embedding' may signify the incorporation of microparticles into the polymer matrix. Formulations with delayed and controlled release of active substance can also be obtained by encapsulation of dispersed microparticles or emulsified microdroplets with the aid of known techniques for coating dispersions and emulsions.

The compounds of the formula (1) can also be used together with at least one further pharmaceutical active substance for combination therapies. To this end, at least one further active substance may be additionally dispersed or dissolved in the composition according to the invention.

The invention also relates to the use of 3-[2-(dimethylamino)methyl-(cyclohex-1-yl)]phenol hydrochloride of formula (1) for preparing a pharmaceutical composition, in particular for the treatment of pain.

The invention thus also relates to a process for treating pain conditions, wherein an effective quantity of 3-[2-(dimethylamino)methyl(cyclohex-1-yl)]phenol hydrochloride of the formula (1) is administered to a patient suffering from pain.

The medicament or pharmaceutical composition according to the invention preferably is suitable for the treatment or inhibition of pain, preferentially pain selected from the group consisting of acute pain, chronic pain, neuropathic pain and visceral pain; of migraine; depressions; neurodegenerative diseases, preferentially selected from the group consisting of Parkinson's disease, Alzheimer's disease, Huntington's disease and multiple sclerosis; cognitive illnesses, preferentially cognitive deficiency conditions, particularly preferably attention-deficit syndrome (ADS), panic attacks; epilepsy; coughing; urinary incontinence; diarrhea; pruritus; schizophrenia; cerebral ischemias; muscular spasms; cramps; food-intake disorders, preferentially selected from the group consisting of bulimia, cachexia, anorexia and obesity; abuse of alcohol and/or drugs (in particular, nicotine and/or cocaine) and/or medicaments; dependence on alcohol and/or drugs (in particular, nicotine and/or cocaine) and/or medicaments, preferentially for the prophylaxis and/or reduction of withdrawal symptoms in the case of dependence on alcohol and/or drugs (in particular, nicotine and/or cocaine) and/or medicaments; development of tolerance phenomena in relation to medicaments, particularly in relation to opioids; gastro-oesophageal reflux syndrome; for diuresis; for antinatriuresis; for influencing the cardiovascular system; for anxiolysis; for heightening wakefulness; for heightening libido, for modulating motor activity and for local anaesthesia.

In particularly preferred manner, the pharmaceutical composition according to the invention is suitable for the treatment and/or inhibition of pain, preferentially of acute pain, chronic pain, neuropathic pain or visceral pain; depressions; epilepsy; Parkinson's disease; abuse of alcohol and/or drugs (in particular, nicotine and/or cocaine) and/or medicaments; dependence on alcohol and/or drugs (in particular, nicotine and/or cocaine) and/or medicaments; preferentially for the prophylaxis and/or reduction of withdrawal symptoms in the case of dependence on alcohol and/or drugs (in particular, nicotine and/or cocaine) and/or medicaments; of the development of tolerance phenomena in relation to medicaments, in particular in relation to opioids, or for anxiolysis.

In quite particularly preferred manner, the medicament according to the invention is suitable for the treatment and/or inhibition of pain, preferentially of acute pain, chronic pain, neuropathic pain or visceral pain.

Particularly preferred is the use of at least one salt according to the invention, in each case optionally in the form of a purified or isolated stereoisomer, in particular enantiomers or diastereomers, or a racemate or in the form of a mixture of stereoisomers, in particular of the enantiomers and/or diastereomers, in an arbitrary mixing ratio, and also, optionally, of one or more pharmaceutically compatible ancillary substances for preparing a pharmaceutical composition for treating and/or inhibiting pain, preferentially pain selected from the group consisting of acute pain, chronic pain, neuropathic pain and visceral pain, or for the treatment and/or inhibition of migraine, depression, neurodegenerative diseases, preferentially a neurodegenerative disease selected from the group consisting of Parkinson's disease, Alzheimer's disease, Huntington's disease and multiple sclerosis, cognitive illnesses, preferentially cognitive deficiency conditions, particularly preferably of attention-deficit syndrome (ADS), panic attacks, epilepsy, coughing, urinary incontinence, diarrhea, pruritus, schizophrenia, cerebral ischemias, muscular spasms, cramps, food-intake disorders, preferentially selected from the group consisting of bulimia, cachexia, anorexia and obesity, abuse of alcohol and/or drugs (in particular, nicotine and/or cocaine) and/or medicaments; dependence on alcohol and/or drugs (in particular, nicotine and/or cocaine) and/or medicaments; preferentially for the prophylaxis and/or reduction of withdrawal symptoms in the case of dependence on alcohol and/or drugs (in particular, nicotine and/or cocaine) and/or medicaments; development of tolerance phenomena in relation to drugs and/or medicaments, particularly in relation to opioids, gastro-oesophageal reflux syndrome, for diuresis, for antinatriuresis, for influencing the cardiovascular system, for anxiolysis, for heightening wakefulness, for heightening libido, for modulating motor activity and for local anaesthesia.

The pharmaceutical composition according to the invention may exist as a liquid, semisolid or solid medicinal form, for example in the form of injection solutions, drops, juices, syrups, sprays, suspensions, tablets, patches, capsules, plasters, suppositories, ointments, creams, lotions, gels, emulsions, aerosols, or in multiparticulate form, for example in the form of pellets or granulates, optionally pressed into tablets, filled in capsules or suspended in a liquid, and may also be administered as such.

In addition to at least one salt according to the invention, optionally in the form of an isolated and/or purified stereoisomer, in particular enantiomers or diastereomers, its racemate or in the form of mixtures of the stereoisomers, in particular of the enantiomers or diastereomers, in an arbitrary mixing ratio, the pharmaceutical composition according to the invention) ordinarily contains further physiologically compatible pharmaceutical ancillary substances, which may preferably be selected from the group consisting of carrier materials, fillers, solvents, diluents, surface-active substances, dyestuffs, preserving agents, disintegrants, lubricating agents, lubricants, flavors and binding agents.

The selection of the physiologically compatible ancillary substances and also the quantities of such substances to be employed depend on whether the pharmaceutical composition is to be administered orally, subcutaneously, parenterally, intravenously, intraperitoneally, intradermally, intramuscularly, intranasally, buccally, rectally or locally, for example onto infections on the skin, of the mucous membranes and in the eyes. Particularly suitable for oral administration are preparations in the form of tablets, dragées, capsules, granulates, pellets, drops, juices and syrups; for parenteral, topical and inhalational application, solutions, suspensions, dry preparations capable of being reconstituted easily and also sprays.

Suitable preparations for percutaneous application include also sustained-release preparations in dissolved form or in a plaster, optionally with addition of agents which promote the penetration of the skin.

Orally or percutaneously administrable forms of preparation are able to release the respective salts according to the invention in delayed manner.

The pharmaceutical compositions according to the invention are prepared using conventional means, appliances and methods, following processes well-known from the state of the art, such as are described, for example, in *Remington's Pharmaceutical Sciences*, editor A. R. Genarro, 17th Edition, Mack Publishing Company, Easton, Pa., 1985, in particular in Part 8, Chapters 76 to 93, which chapters are hereby incorporated by reference as part of the original disclosure.

The quantity of the respective salts according to the invention to be administered to the patient may vary and will depend, for example, on the weight or age of the patient and also on the manner of administration, on the indication and on the degree of severity of the illness. Ordinarily, 0.005 mg/kg to 5000 mg/kg, preferentially 0.05 mg/kg to 500 mg/kg, of body weight of the patient of at least one such compound are applied.

EXAMPLES

Figure 1:
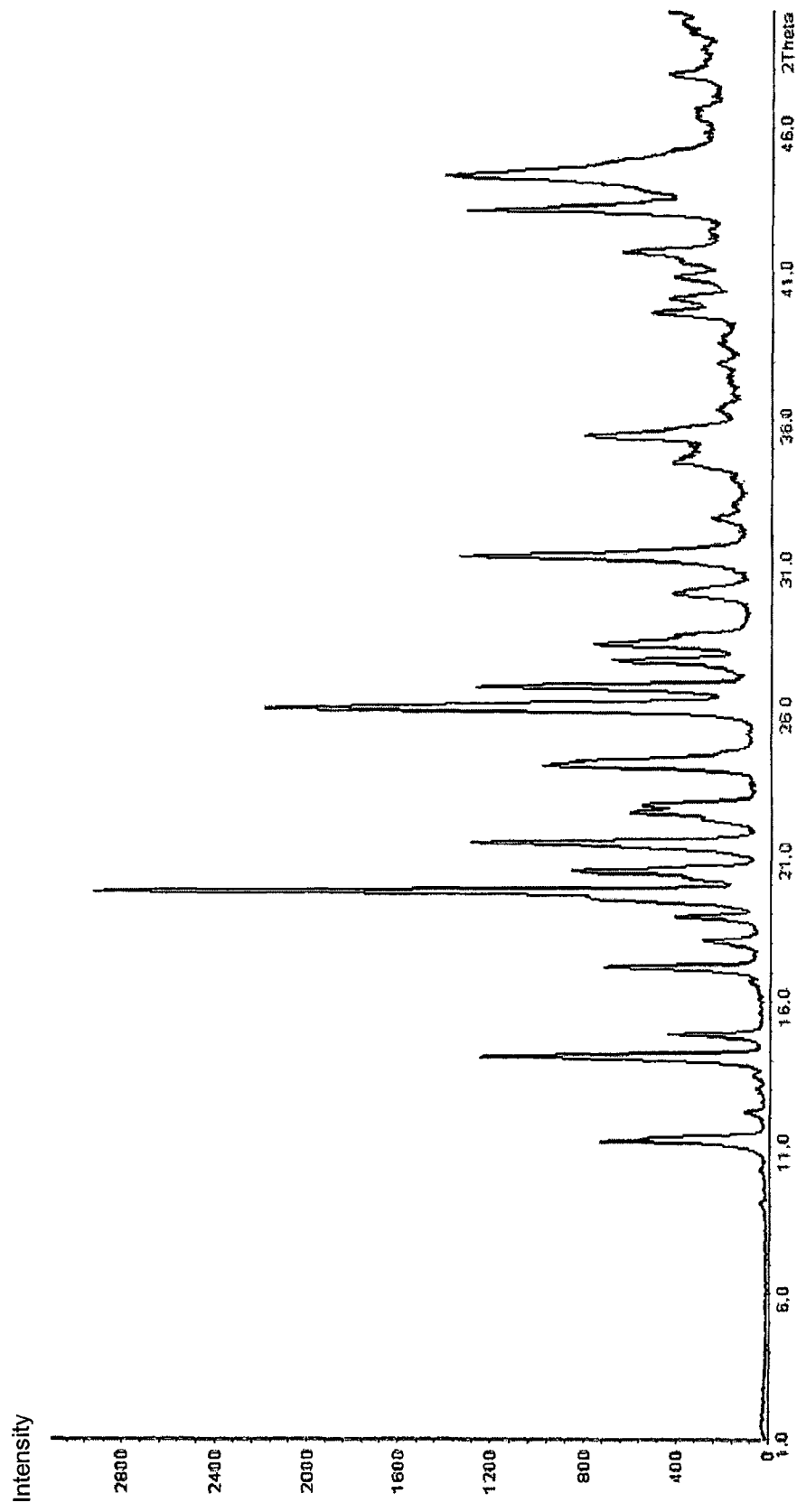
FIG. 1 shows the X-ray diffraction pattern of the polymorphous form I.
Figure 2:
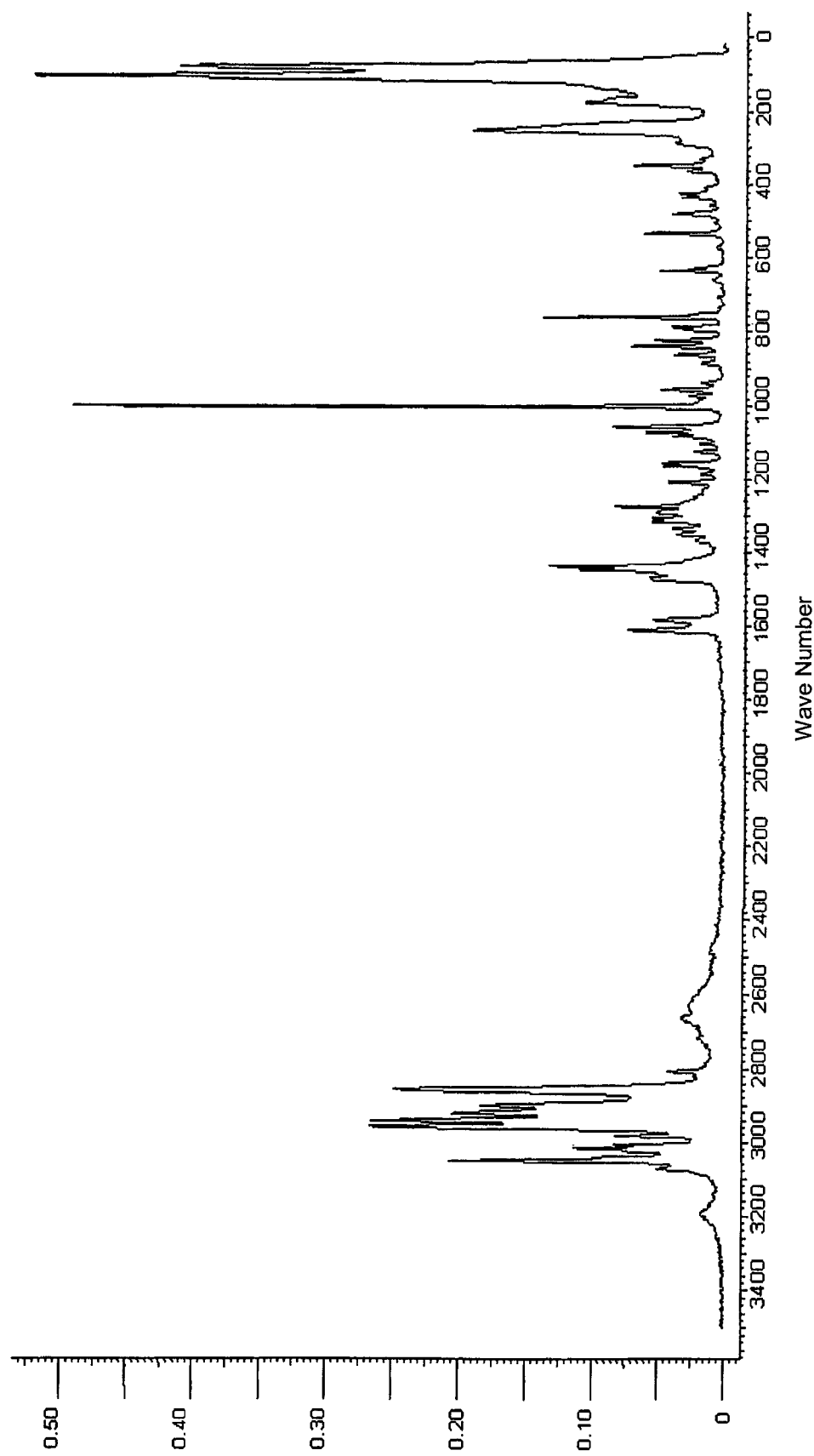
FIG. 2 shows the Raman spectrum of the polymorphous form I.

The following Examples are intended to illustrate the invention in further detail without limiting its scope. Unless state otherwise, all DSC measurements were carried out at a heating-rate of 10° C./minute; the stated temperatures are peak maxima.

Example 0.1

Synthesis of the base
3-[2-(dimethylamino)methyl-(cyclohex-1-yl)]phenol

Procedure a)

In a 1000 ml single-necked flask 52 g (183 mmole) of the precursor 1-(2-(3-methoxyphenyl)cyclohexyl)-N,N-dimethylmethaneamine (purity according to GC: 97.5%, of the trans diastereomer) and 250 ml hydrobromic acid (47%, in water) were charged together and stirred for 2 hours with a magnetic stirrer, subject to reflux. After conclusion of the reaction, the hydrogen bromide was distilled off by applying a vacuum (water-jet pump). The base 3-[2-(dimethylamino)methyl-(cyclohex-1-yl)]phenol was released from the distillation residue with ethyl acetate and aqueous potassium-carbonate solution. The organic phase was dried with $MgSO_4$, and the base 3-[2-(dimethylamino)methyl(cyclohex-1-yl)]phenol was isolated as a yellowish oil (crude yield: 42 g, which corresponded to 98.6% of the theoretical value). The base 3-[2-(dimethylamino)methyl(cyclohex-1-yl)]phenol was added to 250 ml ethyl acetate and stored overnight in a refrigerator. Since no solid substance precipitated out, the solution was inspissated again, whereby strong foaming was observed.

Procedure b)

125 g (440 mmole) of the precursor 1-(2-(3-methoxyphenyl)cyclohexyl)-N,N-dimethylmethaneamine and 500 ml of hydrobromic acid (47%, in water) were introduced together into a single necked flask and stirred under reflux for 2 hours using a magnetic stirrer. After conclusion of the reaction, the hydrogen bromide was distilled off by applying a vacuum (water-jet pump). The distillation residue was added to 250 ml water, and the suspension was covered with a layer of 1000 ml ethyl acetate. The pH of the reaction mixture was adjusted to pH 8 with aqueous sodium-hydroxide solution (c=32% w/w), accompanied by cooling of the reaction mixture with ice. Organic and aqueous phases were separated, the aqueous phase was extracted three times with 350 ml portions of ethyl acetate. In the process, the pH value was monitored and ml water and 27 ml trimethylchlorosilane (TMCS), dissolved in 125 ml acetone, were added. The solid substance that precipitated out was filtered off by suction with a vacuum filter, with application of a vacuum, and then washed with diethyl ether. The yield amounted to 53 g (according to GC analysis 100% of the trans diastereomer).

Further batches of the hydrochloride salt 3-[2-(dimethylamino)methyl-(cyclohex-1-yl)]phenol hydrochloride were prepared in an analogous manner:

| Batch | Precursor/g | HBr (47%)/ml | Base/g | Acetone/ml | Water/ml | TMCS (in acetone)/ml | Yield/g | Trans diastereomer/% |
|---|---|---|---|---|---|---|---|---|
| 1-12 | 129 | 520 | 109 | 550 | 4.5 | 55.7 (275) | 124 | 98.8 |
| 1-13 | 143 | 600 | 117 | 585 | 5 | 63.5 (290) | 119 | 98.6 |
| 1-14 | 121 | 520 | 101 | 500 | 4 | 55 (250) | 119 | 98.7 |
| 1-15 | 163 | 650 | 130 | 650 | 6 | 72 (325) | 153 | 97.4 |
| 1-16 | 148 | 600 | 121 | 610 | 5.5 | 65.5 (300) | 138 | 98.8 | maintained at a value of at least pH 8 using aqueous sodium-hydroxide solution (c=32% w/w). The mixture was extracted two more times with 150 ml portions of ethyl acetate, and the organic phase was dried with $MgSO_4$. The solvent was removed in a rotary evaporator (bath temperature 44° C., vacuum <20 mbar). The yield of crude product 3-[2-(dimethylamino)methyl(cyclohex-1-yl)]phenol amounted to 101 g. The crude product 3-[2-(dimethylamino)methyl(cyclohex-1-yl)]phenol was added to 100 ml acetone and stirred until the light-brown material solidified. Subsequently the material was filtered out by suction and washed with a little diethyl ether. The yield amounted to 48%, relative to the quantity of crude product employed.

Example 0.2

Preparation of 3-[2-(dimethylamino)methyl(cyclohex-1-yl)]phenol hydrochloride

In order to prepare the hydrochloride salt, 42 g of the base 3-[2-(dimethylamino)methyl(cyclohex-1-yl)]phenol were added to 210 ml methyl ethyl ketone. Subsequently 2 ml water and 23 ml trimethylchlorosilane, dissolved in 45 ml methyl ethyl ketone, were added. The reaction mixture was cooled down to 0° C. by cooling with ice and was kept cold overnight (in a refrigerator at about 4° C.). The solid substance that precipitated out was filtered out by suction using a suction filter, with application of a vacuum, and then washed with 30 ml of acetone. The yield of 3-[2-(dimethylamino)methyl(cyclohex-1-yl)]phenol hydrochloride was 49 g (corresponding to 100% of the theoretical value). According to NMR and GC analyses, the produce was >95% trans diastereomer. The melting-point was 122-126° C.

Example 1a

Preparation of (1R,2R)-3-[2-(dimethylamino)methyl-(cyclohex-1-yl)]phenol hydrochloride In order to prepare the hydrochloride salt, 48.5 g (208 mmole) of the base 3-[2-(dimethylamino)methyl(cyclohex-1-yl)phenol, prepared as in Example 0.1, were added to 250 ml acetone in accordance with Procedure b). Subsequently 2

The solid substances of batches 1-12 to 1-16 were combined and intimately blended. In order to remove residual solvent (acetone and diethyl ether), the combined solids were predried (1 day at room temperature under vacuum <150 mbar), and subsequently dried over Sicacide for 6 days at 70° C. and under a vacuum of <20 mbar. According to GC analysis, the proportion of residual solvent (acetone, diethyl ether) amounted to less than 200 ppm in each instance.

Example 1b

Preparation of (1R,2R)-3-[2-(dimethylamino)methyl-(cyclohex-1-yl)]phenol hydrochloride In a 100 liter double-walled reactor with electric impeller stirrer, Pt100 temperature-measuring device and oil-based cooling/heating system, 37 kg (137.12 mol) of (1R,2R)-3-(2-dimethylaminomethylcyclohexyl)phenol hydrochloride were dissolved in 55 l water at a stirring speed of 100 rpm. The solution was heated to 40° C.-60° C. until a clear solution arose. At reduced pressure (about 30-50 mbar), 38 l-41 l of the water were removed. The solution was stirred at 7° C. for about 16 hours. The resulting suspension was separated out via a centrifuge. The product was dried in a drying cabinet at 45° C. for 18 hours under a vacuum up to a final pressure of 130 mbar. 25.9 kg (70% of the theoretical value) of (1R,2R)-3-(2-dimethylaminomethylcyclohexyl)phenol hydrochloride were obtained with a residual-water content of 5.9%.

Example 2

Preparation of amorphous (1R,2R)-3-[2-(dimethylamino)-methyl(cyclohex-1-yl)]phenol hydrochloride Example 2.1

Freeze Drying 500.4 mg of the hydrochloride prepared in accordance with Example 1b were dissolved in 5 ml water and then chilled to −74° C. The solution was then freeze dried at this temperature and at a pressure of <0.1 mbar for 20 hours. A solid, white residue was obtained quantitatively which, according to evaluation of the Raman spectrum, is amorphous.

Example 2.2

Freeze Drying 212.5 mg of the hydrochloride prepared in accordance with Example 1b were dissolved in 2 ml water and then chilled to −89° C. The solution was then freeze dried at this temperature and at a pressure of <0.01 mbar for 66 hours. A solid, white residue was obtained quantitatively, which, according to evaluation of the Raman spectrum, is amorphous.

Example 2.3

Freeze Drying 651.5 mg of the hydrochloride prepared in accordance with Example 1b were dissolved in 6.5 ml water and then chilled to −80° C. The solution was then freeze dried at this temperature and at a pressure of 0.6 mbar for 21 hours. A solid, white residue was obtained quantitatively, which, according to evaluation of the Raman spectrum, is amorphous.

Example 3

Preparation of (1R,2R)-3[-2-(dimethylamino)methyl-(cyclohex-1-yl)]phenol hydrochloride as crystalline form I Example 3.1

209.7 mg of the hydrochloride prepared in accordance with Example 1a were suspended in 6 ml ethyl acetate and stirred for ten days at a stirrer speed of approximately 600 rpm (revolutions per minute) and at a temperature from 23° C. to 28° C., whereby the temperature for the first two days was 23° C., for the next two days was 28° C., and for the remaining duration 23° C. The resulting white solid substance was separated out and analyzed. According to the Raman spectrum, only bands of the crystalline form I were measured.

Example 3.2

101.4 mg of the hydrochloride prepared in accordance with Example 1a were suspended in 3 ml ethyl acetate, added to 14.5 mg of the hydrochloride in the crystalline form I and stirred for ten days at a stirrer speed of approximately 600 rpm (revolutions per minute) and at a temperature of 23° C. The resulting white solid substance was separated out by vacuum filtration (5 minutes) and dried in air. According to the X-ray powder diffractogram, only signals of the crystalline form I were measured. A melting-point of approximately 150° C. was ascertained by differential scanning calorimetry (DSC, heating-rate 10° C./minute). An endothermic peak is observed within the range from 121° C. to 122° C.

Example 4

Preparation of (1R,2R)-3-[2-(dimethylamino)methyl-(cyclohex-1-yl)]phenol hydrochloride as crystalline form II Example 4.1

191.8 mg of the hydrochloride prepared in accordance with Example 1b were heat-treated for 23.5 hours in an open vessel at 155° C. According to the X-ray powder diffractogram, only signals of the crystalline form II are measured. A melting-point of approximately 177° C. is ascertained by differential scanning calorimetry (DSC, heating-rate 10° C./minute).

Example 4.2

600 mg of the hydrochloride of the crystalline form III were added to 100 mg of the hydrochloride in the crystalline form II, intimately blended, and suspended in 10 ml of ethyl acetate. The suspension was stirred for six days at room temperature. The resulting white solid substance was separated out by vacuum filtration and dried for 1.5 hours in a drying cabinet at a temperature of 45° C. and under a vacuum <150 mbar. According to DSC analysis (heating-rate 10 K/minute), the resulting solid substance exhibits an endothermy at 177.2° C., which is associated with the crystalline form II.

Example 4.3

4.0 g hydrochloride of the crystalline form V were stirred in a vessel without solvent at a temperature of 154° C. (temperature of the oil bath 154° C. to 162° C.). The Raman spectrum of the resulting solid substance exhibits only bands of the crystalline form II.

Example 5

Preparation of (1R,2R)-3-[2-(dimethylamino)methyl-(cyclohex-1-yl)]phenol hydrochloride as crystalline form III Example 5.1

76.9 mg of the amorphous hydrochloride prepared in accordance with Example 2 were suspended in 1 ml ethyl acetate and stirred for three days at a stirrer speed of approximately 400 rpm (revolutions per minute) and at a temperature of 25° C., for one day at 40° C., for one day at 60° C., for one day at 50° C., for one day at 45° C., for one day at 70° C., and for 9 days at 75° C., whereby starting from the third day the stirring speed was 600 rpm in each instance. The resulting white solid substance was separated out by vacuum filtration (about 5 minutes) and dried in air. According to the X-ray powder diffractogram, only signals of the crystalline form III are measured.

Example 5.2

70.5 mg of the amorphous hydrochloride prepared in accordance with Example 2 were suspended in 1.5 ml tert.-butylmethyl ether and stirred for seven days at a stirrer speed of approximately 600 rpm (revolutions per minute) and at a temperature of 40° C. The resulting white solid substance was separated by vacuum filtration (about 5 minutes) and dried in air. According to the Raman spectrum, only bands of the crystalline form III were measured. A glass transition temperature between 66° C. and 67° C. and a melting-point of approximately 155° C. were ascertained by differential scanning calorimetry (DSC, heating-rate 10° C./minute). A further endothermic peak was observed at 88° C.

Example 5.3

147.8 mg of the amorphous hydrochloride prepared in accordance with Example 2 were suspended in 1.5 ml ethyl acetate and stirred for one day at a stirrer speed of approximately 600 rpm (revolutions per minute) and at a temperature of 40° C. The resulting white solid substance was separated by vacuum filtration (about 5 minutes) and dried in air. According to the Raman spectrum, only bands of the crystalline form III were measured.

Example 5.4

1 g of an acetone solvate or ethanol solvate of the hydrochloride is suspended in 18 ml ethyl acetate and stirred at a temperature of 23° C. The white solid substance is separated off by vacuum filtration (5 minutes) and dried in air. According to the Raman spectrum, only bands of the crystalline form III are measured.

Example 6

Preparation of (1R,2R)-3-[2-(dimethylamino)methyl (cyclohex-1-yl)]phenol hydrochloride as crystalline form IV Example 6.1

178.2 mg of the amorphous hydrochloride prepared in accordance with Example 2 were suspended in 3.6 ml tert.-butylmethyl ether and stirred for one day at a stirrer speed of approximately 600 rpm (revolutions per minute) and at a temperature of 40° C. The resulting white solid substance was separated by vacuum filtration (about 5 minutes) and dried in air. According to the X-ray powder diffractogram, only lines of the crystalline form IV were measured. A slight exothermy is observed by differential scanning calorimetry (DSC, heating-rate 10° C./minute) at about 122° C., which indicates a monotropic conversion into another form. In the further course of the DSC experiment, initially an endothermic peak at approximately 162° C., and a further peak at approximately 171° C., were observed.

Example 6.2

153.2 mg of the amorphous hydrochloride prepared in accordance with Example 2 were suspended in 3.5 ml heptane and stirred for 26 days at a stirrer speed of approximately 600 rpm (revolutions per minute) and at a temperature within the range from 40° C. to 90° C., whereby the temperature for the first eight days was 40° C., for the next six days 50° C., for one day 75° C., for three days 80° C., and for eight days 90° C. The white solid substance was separated by centrifuging (10 minutes at 10,000 revolutions) and dried in air. According to the Raman spectrum, only bands of the crystalline form IV were measured.

Example 6.3

4.0 g hydrochloride of the crystalline form III were stirred in a 100 ml round-necked flask without solvent for five hours at a temperature of 154° C. (temperature of the oil bath 154° C. to 162° C.).

Upon DSC analysis (heating-rate 100K/minute), the resulting solid substance exhibits an endothermy at 168.8° C., which is associated with the crystalline form IV.

Example 7

Preparation of (1R,2R)-3-[2-(dimethylamino)methyl (cyclohex-1-yl)]phenol hydrochloride as crystalline form V Example 7.1

53.7 mg of the hydrochloride prepared in accordance with Example 1b were dissolved in 1 ml ethanol and water (volume ratio: 1:1) at room temperature and left to stand in air at room temperature until the solvent mixture had completely evaporated and a solid substance remained. According to the X-ray powder diffractogram, only lines of the crystalline form V were measured. The solid residue was therefore determined to be the crystalline form V.

Example 8

Stability at Room Temperature

Example 8.1

51.4 mg of the hydrochloride in the crystalline form 1 and 49.8 mg of the hydrochloride in the crystalline form II were suspended in 2 ml ethyl acetate and stirred for eleven days at a temperature of 25° C. The solid substance was separated by vacuum filtration and dried in air. According to the Raman spectrum, the sample predominantly contained the crystalline form I and small amounts of form V.

Example 8.2

33.6 mg of the hydrochloride in the crystalline form III and 31.5 mg of the hydrochloride in the crystalline form IV were suspended in 2 ml ethyl acetate and stirred for twelve days at a temperature of 23° C. The solid substance was separated by vacuum filtration and dried in air. According to the Raman spectrum, only bands of the crystalline form I were measured.

Example 8.3

30.6 mg of the hydrochloride in the crystalline form III and 30.7 mg of the hydrochloride in the crystalline form II are suspended in 2 ml ethyl acetate and stirred for three days at a temperature of 23° C. The white solid substance is separated off by vacuum filtration and dried in air. According to the Raman spectrum, only bands of the crystalline form II are measured.

Example 8.4

31.1 mg of the hydrochloride in the crystalline form IV and 28.9 mg of the hydrochloride in the crystalline form II are suspended in 2 ml ethyl acetate and stirred for 32 days at a temperature of 23° C. The white solid substance is separated out by vacuum filtration and dried in air. According to the Raman spectrum, initially only bands of the crystalline form II were measured. After the first three days of the experiment had passed, the first traces of the crystalline form I were detected, and after 32 days almost exclusively the crystalline form I was detected.

From Examples 8.1 to 8.4, for the stability of the crystalline compounds I, II, III and IV at room temperature under conditions for avoiding the formation of solvates this sequence arises: I>II>III≈IV.

Example 9

Absorption of Water

The absorption of water is ascertained by dynamic vapour sorption (DVS) with a DVS-1 instrument manufactured by Surface Measurement Systems Ltd. The sample is placed in a platinum crucible at the pivot of a microbalance. The sample is then initially equilibrated at 50% relative air humidity and then subjected to a predefined measuring program. The temperature was 25° C. The change in weight of the sample is determined.

A) Crystalline Form I

The crystalline form absorbs water very quickly at a relative air humidity >50%. If the relative air humidity is reduced to 0%, the water content of the sample is reduced to 3.2 wt. %. The water content at 50% relative air humidity at the end of the measuring cycle is 7.2%, and the recorded Raman spectrum corresponds to the Raman spectrum of the crystalline form V.

B) Crystalline Form II

The crystalline form absorbs water very quickly at a relative air humidity >75%. If the relative air humidity is reduced to 0%, the water content of the sample is reduced to 3.3 wt. %. The water content at 50% relative air humidity at the end of the measuring cycle is 7.9%, and the recorded Raman spectrum corresponds to the Raman spectrum of the crystalline form V.

C) Crystalline Form III

The crystalline form absorbs water very quickly at a relative air humidity >55%. If the relative air humidity is reduced to 0%, the water content of the sample is reduced to 3.1 wt. %. The water content at 50% relative air humidity at the end of the measuring cycle is 7.8%, and the recorded Raman spectrum corresponds to the Raman spectrum of the crystalline form V.

D) Crystalline Form IV

The crystalline form absorbs water very quickly at a relative air humidity >60%. If the relative air humidity is reduced to 0%, the water content of the sample is reduced to 3.1 wt. %. The water content at 50% relative air humidity at the end of the measuring cycle is 7.6%, and the recorded Raman spectrum corresponds to the Raman spectrum of the crystalline form V.

Example 10

Humid Storage of the Crystalline Forms II and III

Storage conditions: 25° C. and 60% relative air humidity for 5 hrs, 24 hrs and 7 days
Test Conditions:
First Test Series:

The substances were weighed directly into DSC and TGA crucibles, and these crucibles were stored in a climate chamber.
Second Test Series:

50 mg of the substances were weighed into 1 ml vials, three times in each case, and these vials were then stored openly in a climate chamber.

The two crystalline forms II and III display differing water-absorption behavior. Modification II absorbs water more slowly in both tests than modification III. Whereas, after 5 hours, modification III has already absorbed 6.70% water in the first test series, and 1.92% water in the second test series, in the case of modification II no appreciable absorption of water can be established (0.04% and 0.12%, respectively).

After 24 hours, in the case of modification III in the first test series the water equivalent has not increased further (6.28%), whereas in the second test series after 24 hours a rise in the water content to 6.08% has occurred. On the other hand, after 24 hours in the first test series, modification II has absorbed 3.28% water, and in the second test series 6.08% water.

After one week of storage at 60% relative air humidity, in the case of modification III—both in the first test series and in the case of the second test series—no significant absorption of water can any longer be registered (water content: 6.74% and 6.83%, respectively). In the case of modification II, a water content of 7.03% and 7.04%, respectively, arises after one week in both test series.

Example 11

Example 11.1

Formation of Ethanol Solvate 67.1 mg of the hydrochloride prepared in accordance with Example 1b are stirred in suspension in 0.25 ml ethanol at 25° C. for one day. According to Raman and TG-FTIR analyses, an ethanol solvate is present.

The loss of mass determined by TG-FTIR amounted to 8.9%, whereby ethanol and a little water were detected.

Example 11.2

Formation of Ethanol Solvate 99.7 mg of the hydrochloride prepared in accordance with Example 1b are stirred in suspension in 0.2 ml ethanol at 25° C. for one day. According to Raman analyses, an ethanol solvate is present.

Storage of the solvate obtained in such a way at room temperature in a vacuum overnight does not result in desolvation. Further storage of the sample for 2 months in the presence of a saturated $Mg(NO_3)_2$ solution and subsequent storage for 2 months in the presence of a saturated NaCl solution resulted in the hydrate form V.

Example 11.3

Formation of Acetone Solvate 100 mg of the hydrochloride prepared in accordance with Example 1b were heat-treated for 23.5 hours at 155° C. As Raman analysis shows, form II arose. 51 mg of the material obtained in this way were suspended in 0.1 ml of an acetone/water mixture (95:5 volume/volume) at 25° C. for 2 days. Raman analysis showed the formation of a solvated form. The loss of mass determined by TG-FTIR amounted to 9.4%, whereby acetone and a little water were detected.
Instruments and Methods
Differential Scanning Calorimetry (DSC):

Instrument designation Perkin Elmer DSC 7 or Perkin Elmer Pyris 1. Variable measurements (heating-rate) in gold or aluminium crucibles.

Mettler Toledo DSC 821, perforated 40 μm aluminium standard crucible, variable temperature range and variable heating-rate, nitrogen atmosphere.

Unless otherwise stated, amounts of material within the range from 2 mg to 20 mg were employed.
Powder X-Radiation Diffraction (PXRD) Patterns:

PXRD is carried out with a Philips 1710 powder X-radiation diffractometer or with a Phillips X'Pert PW 3040, using $CuK_\alpha$ radiation. D-spacings are computed from the 2θ values, the wavelength of 1.54060 Å being used as a basis. The 2θ values generally have an error-rate of +0.1-0.2°. The experimental error in the case of the D-spacing values is therefore dependent on the location of the peak.
Raman Spectroscopy:

FT Raman spectra are recorded with a Bruker RFS 100 FT Raman system which is operated with an Nd:YAG laser (wavelength 1064 nm) and with a germanium detector cooled with liquid nitrogen. For each sample, 64 scans with a resolution of 2 cm$^{-1}$ are accumulated. A laser power of 100 mW is generally used.

TG-FTIR

Netsch Thermo-Microbalance TG209 with Bruke FT-IR Spektrometer Vektor 22. The measurements were carried out in an aluminium crucible (open or with microhole) under nitrogen atmosphere. The heating-rate amounted to 10 K/minute within a range of 25-250° C.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A crystalline salt of hydrogen chloride and 3-[2-(dimethylamino)methyl-(cyclohex-1-yl)]phenol, wherein said 3-[2-(dimethyl-amino)methyl-(cyclohex-1-yl)]phenol is in the form of an enantiomer with a (1R,2R) absolute configuration, and said salt is crystalline form II and exhibits a characteristic X-ray diffraction pattern within the range from 2° to 35° 2θ with pronounced characteristic lines corresponding to the following 2theta values: 11.1 (m), 12.9 (w), 16.1 (m), 17.1 (w), 19.1 (s), 19.6 (w), 19.9 (m), 23.2 (w), 25.8 (w), 26.1 (s), and 33.6 (w).

2. A crystalline salt according to claim 1, wherein said salt is 3-[2-(dimethylamino)methyl-(cyclohex-1-yl)]phenol hydrochloride corresponding to formula (1)

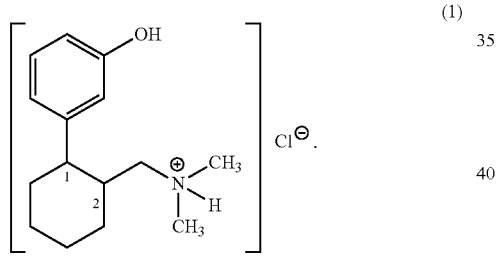

Figure 3:
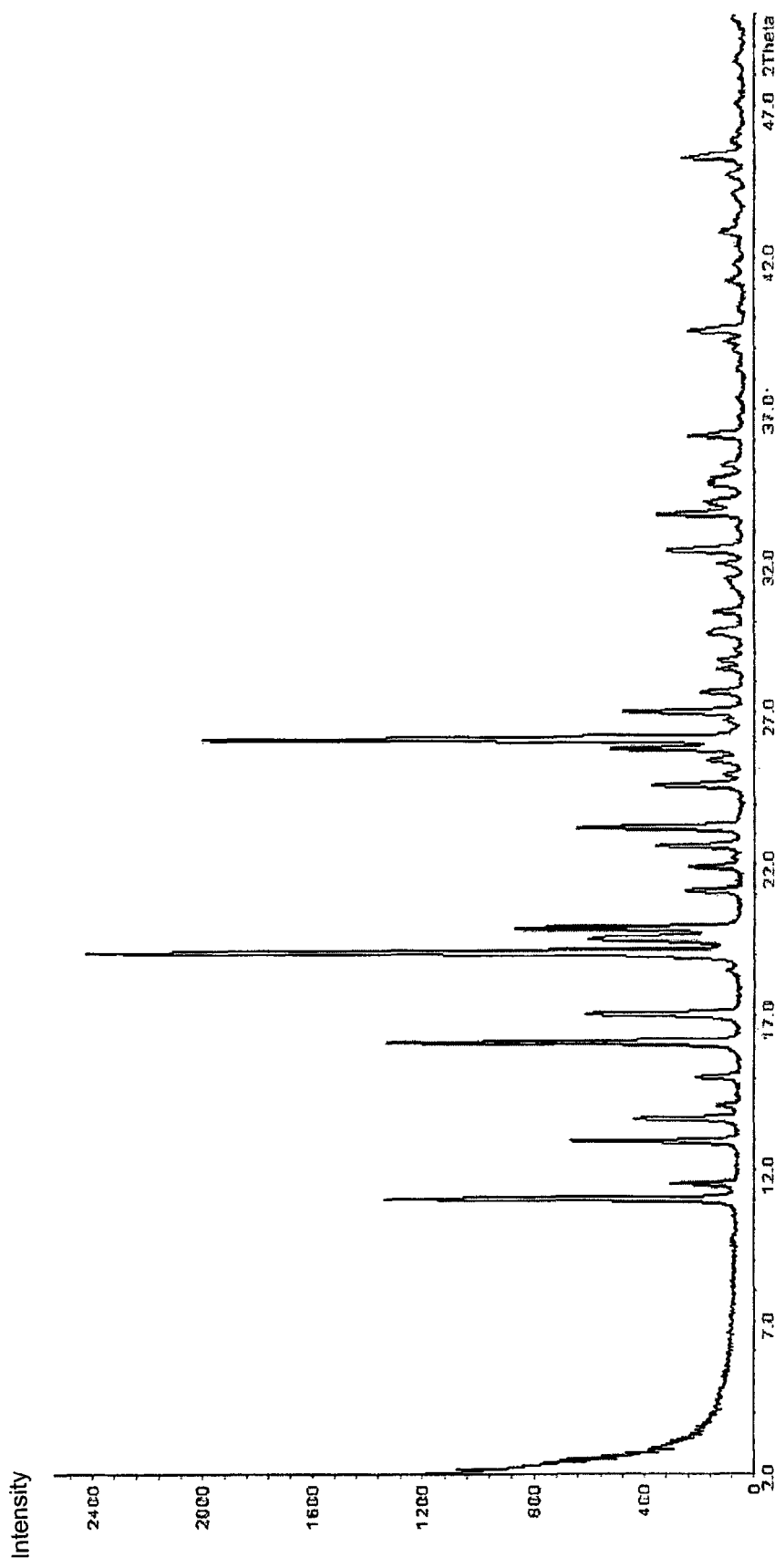
FIG. 3 shows the X-ray diffraction pattern of the polymorphous form II.

3. A crystalline salt of hydrogen chloride and 3-[2-(dimethylamino)methyl-(cyclohex-1-yl)]phenol, wherein said 3-[2-(dimethyl-amino)methyl-(cyclohex-1-yl)]phenol is in the form of an enantiomer with a (1R,2R) absolute configuration, and said salt is crystalline form II and exhibits the X-ray diffraction pattern of FIG. 3.

Figure 4:
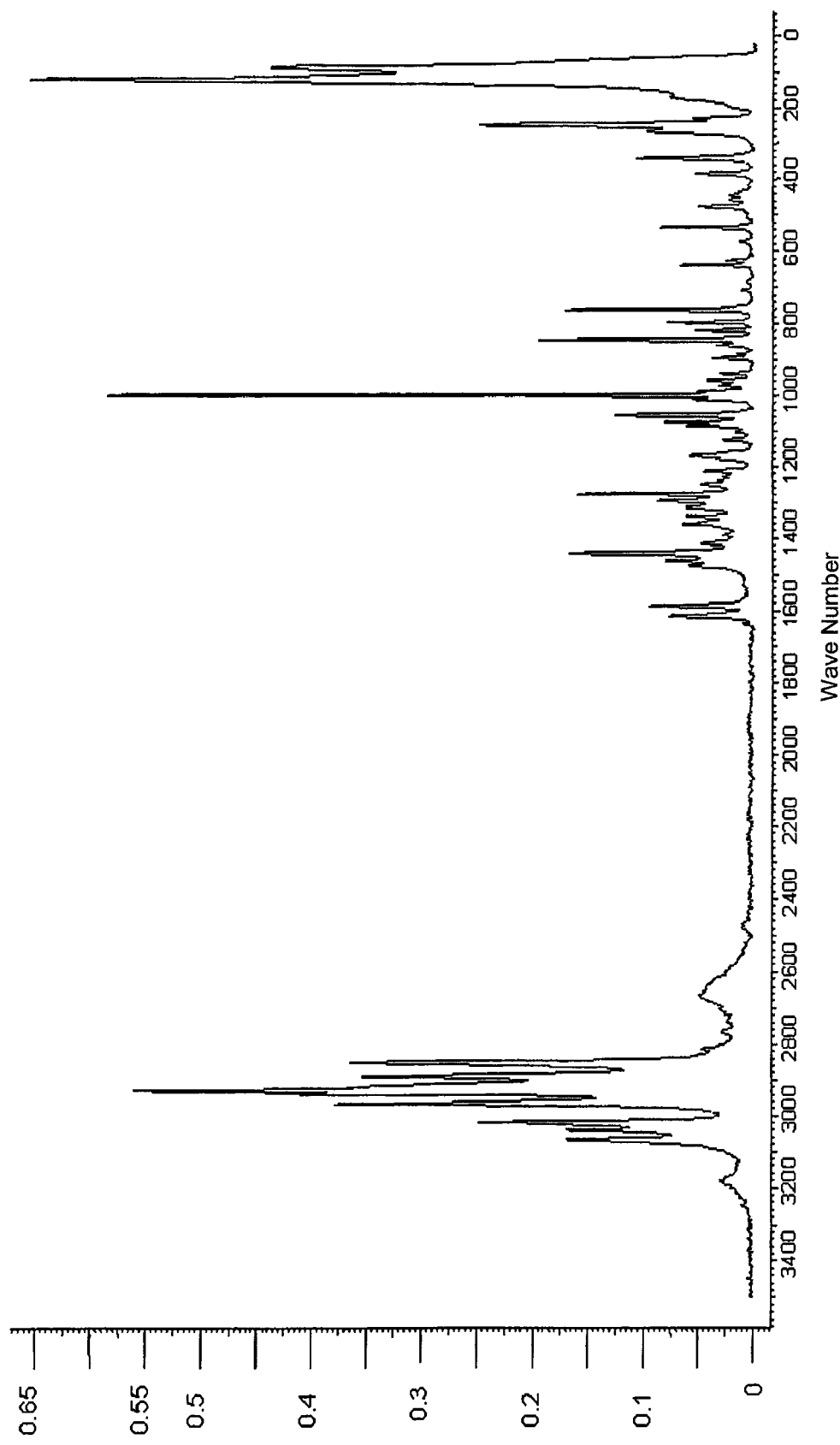
FIG. 4 shows the Raman spectrum of the polymorphous form II.
Figure 5:
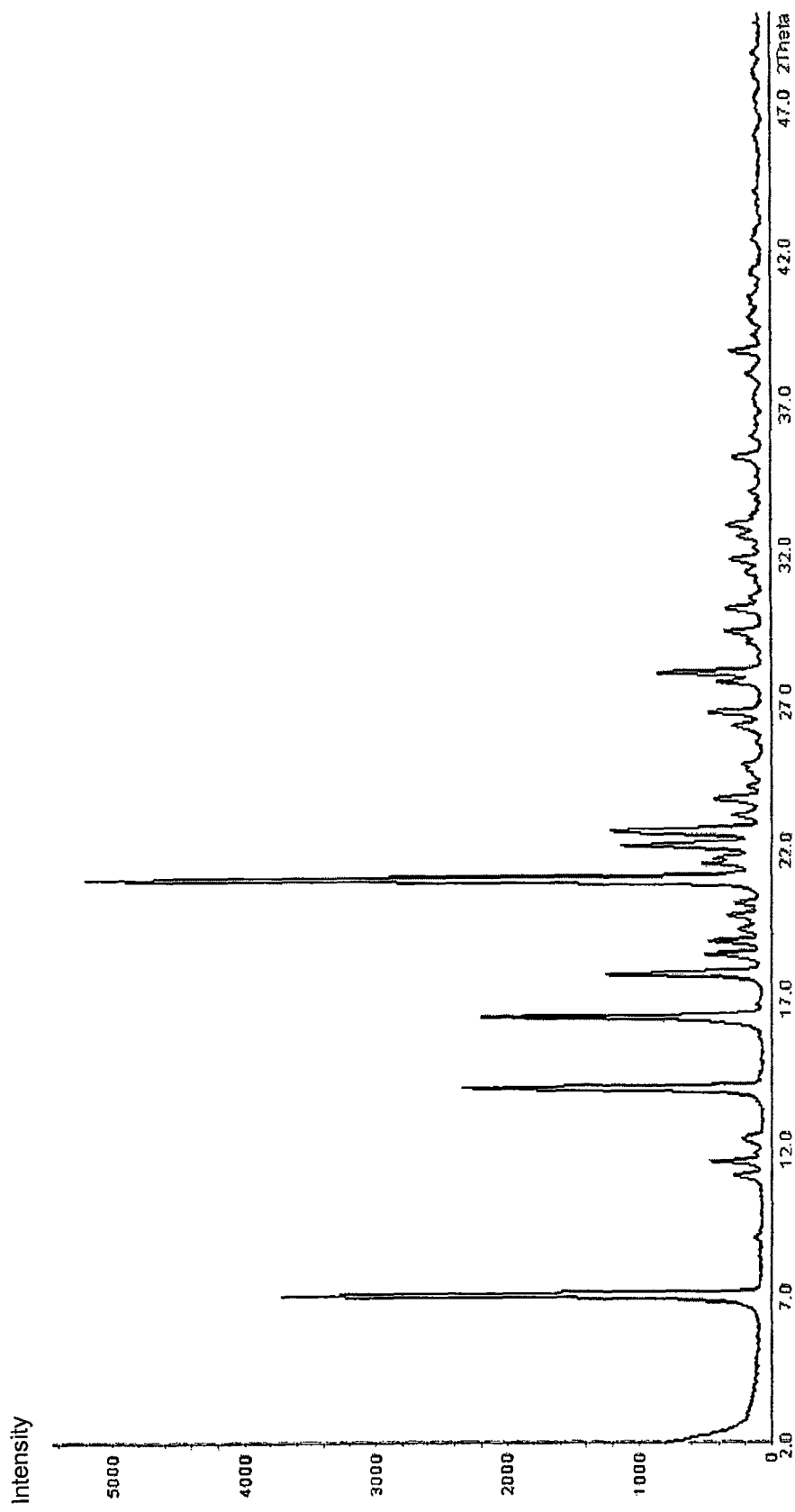
FIG. 5 shows the X-ray diffraction pattern of the polymorphous form III.
Figure 6:
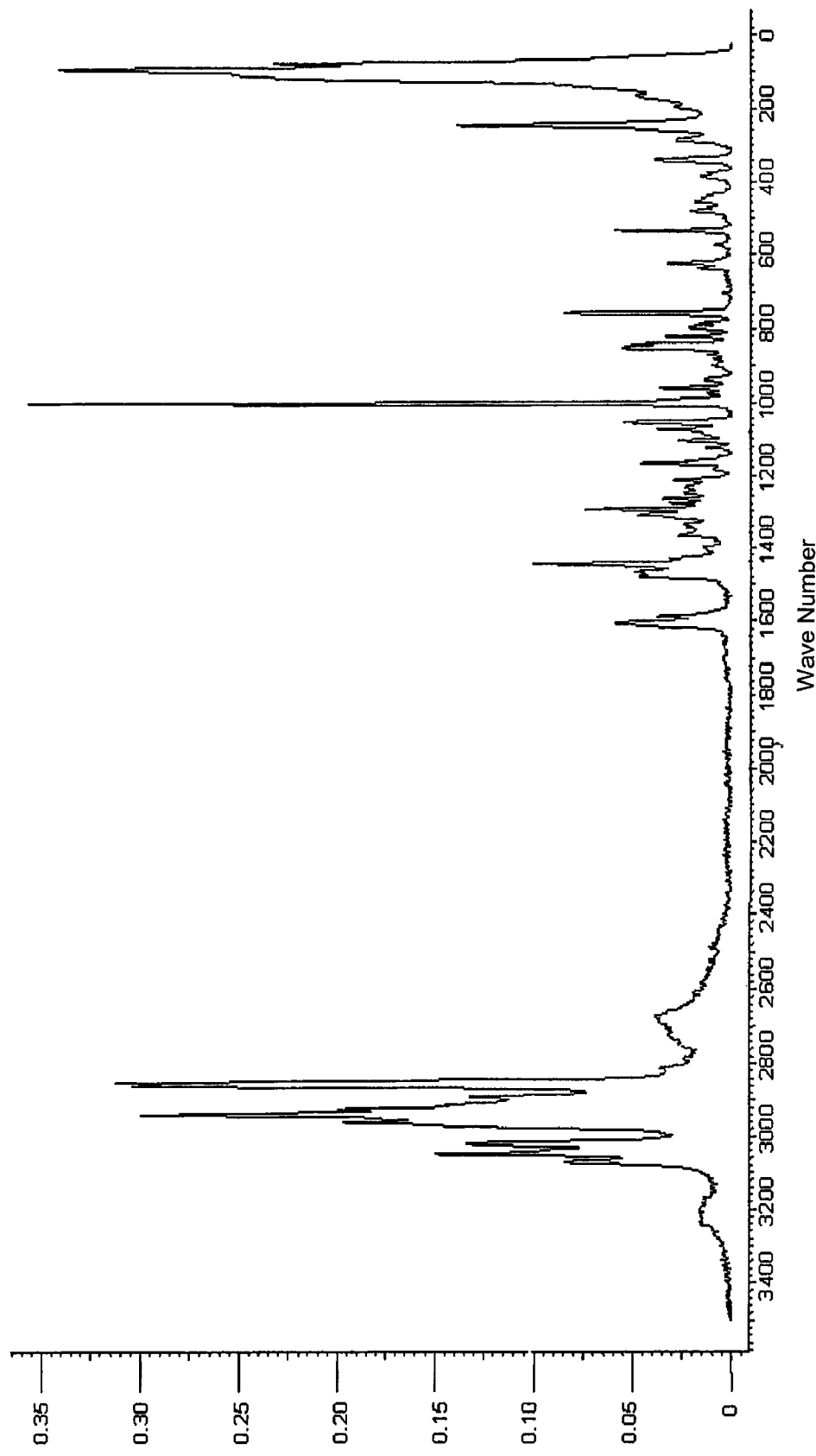
FIG. 6 shows the Raman spectrum of the polymorphous form III.
Figure 7:
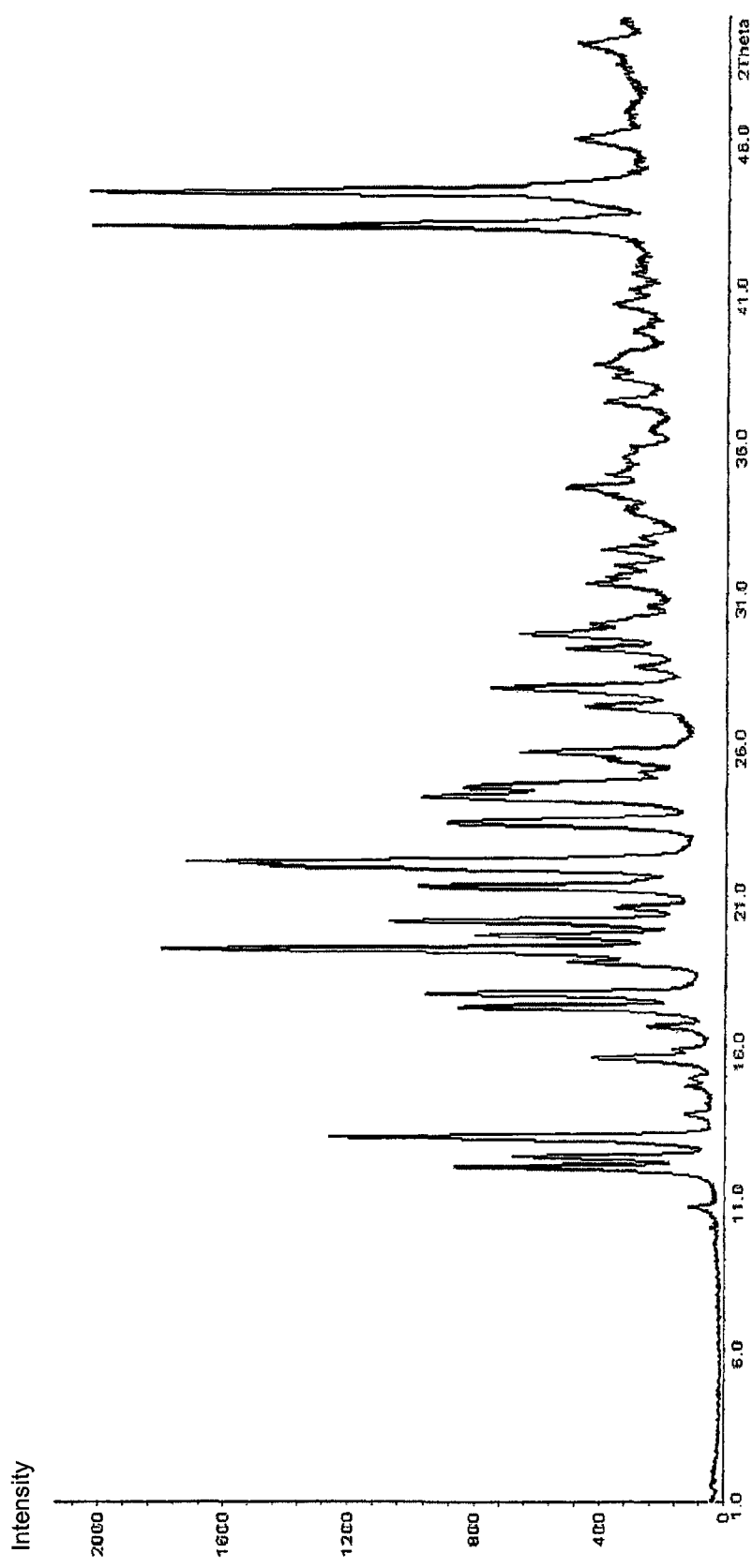
FIG. 7 shows the X-ray diffraction pattern of the polymorphous form IV.
Figure 8:
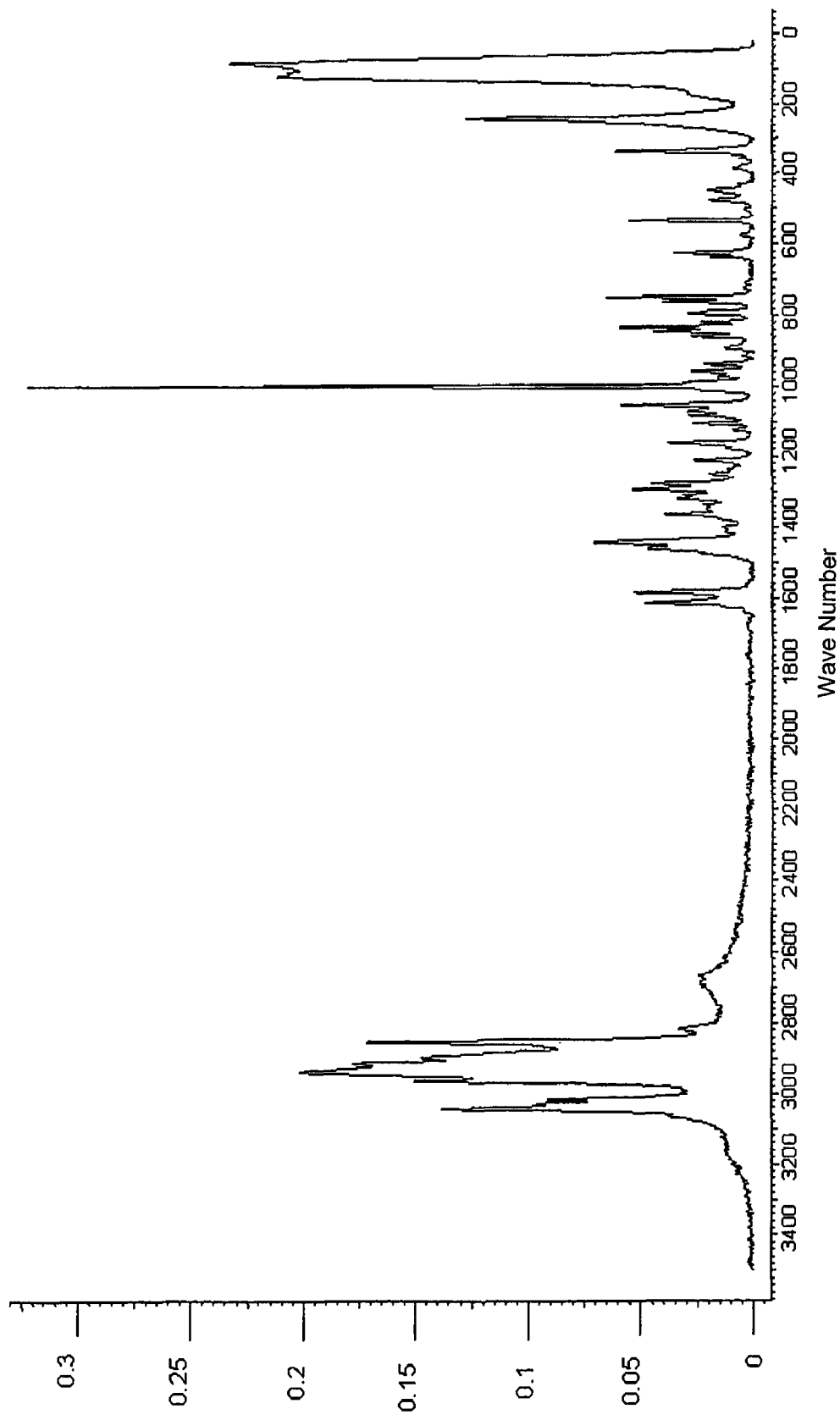
FIG. 8 shows the Raman spectrum of the polymorphous form IV.
Figure 9:
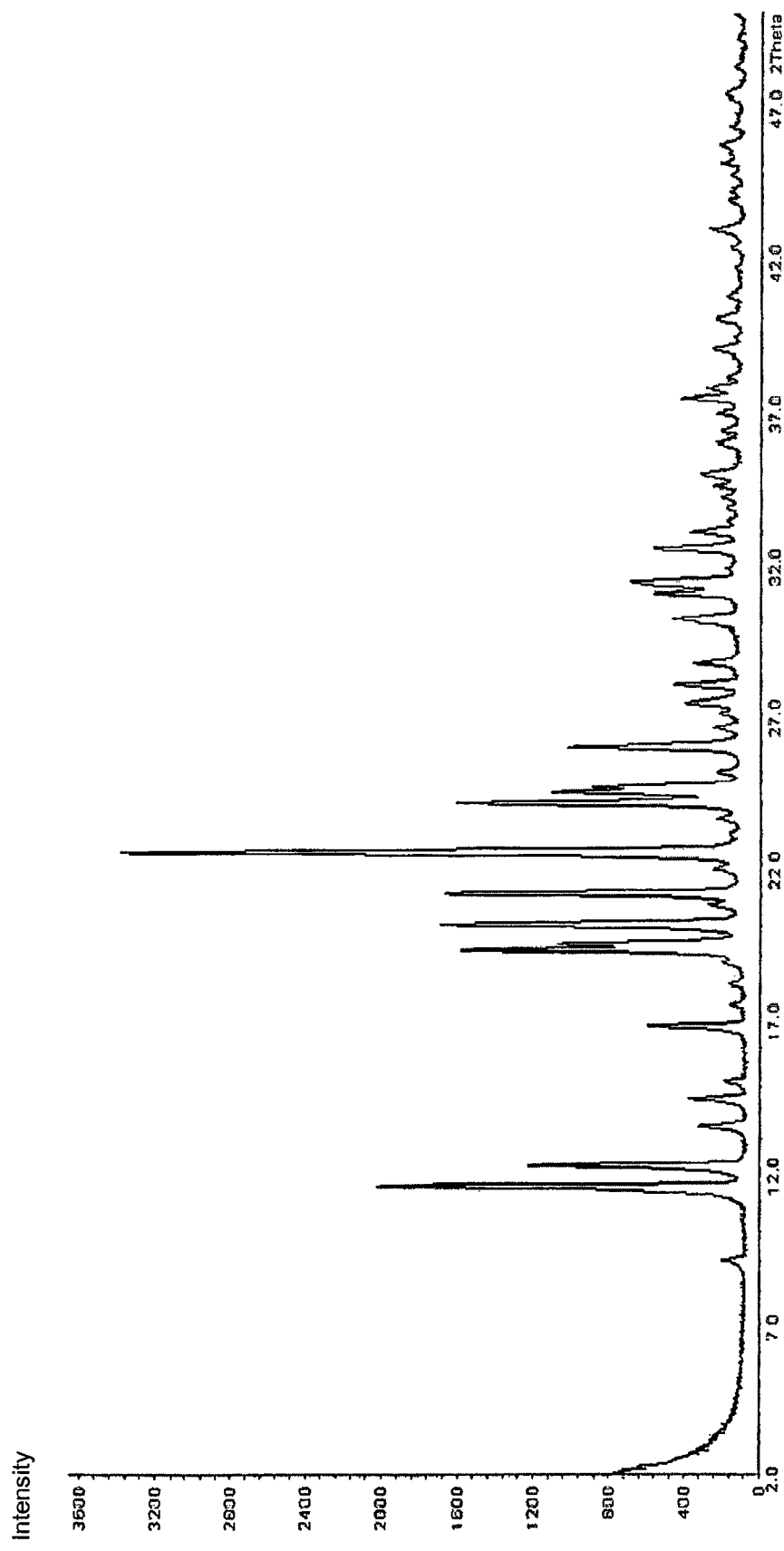
FIG. 9 shows the X-ray diffraction pattern of the polymorphous form V.
Figure 10:
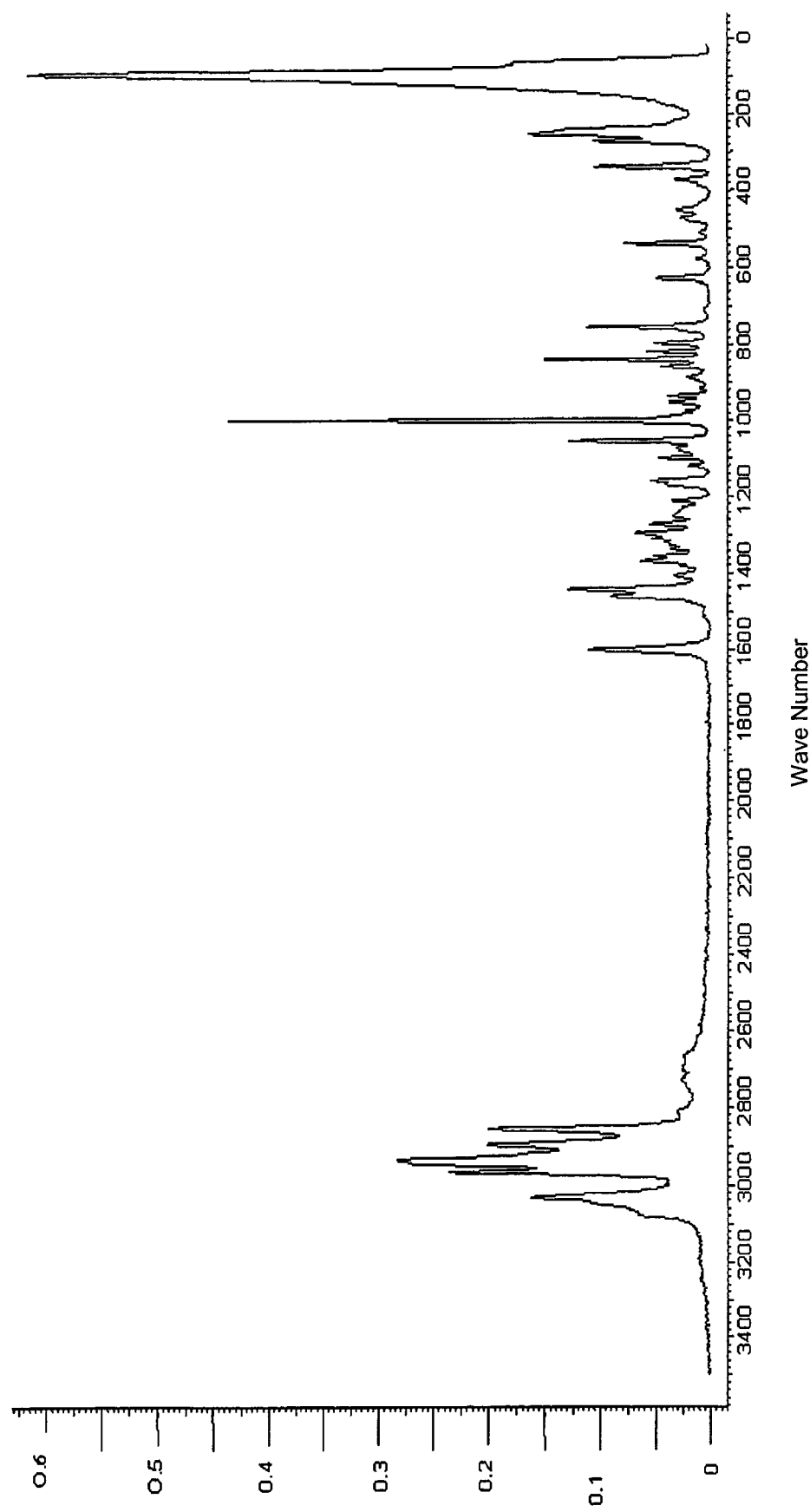
FIG. 10 shows the Raman spectrum of the polymorphous form V.

4. A crystalline salt of hydrogen chloride and 3-[2-(dimethylamino)methyl-(cyclohex-1-yl)]phenol, wherein said 3-[2-(dimethyl-amino)methyl-(cyclohex-1-yl)]phenol is in the form of an enantiomer with a (1R,2R) absolute configuration, and said salt is crystalline form II and exhibits the Raman spectrum of FIG. 4.

5. A process for preparing crystalline form II of 3-[2-(dimethylamino)methyl-(cyclohex-1-yl)]phenol hydrochloride according to claim 1, said process comprising:
 a) heat treating crystalline form IV of 3-[2-(dimethylamino)methyl(cyclohex-1-yl)]phenol hydrochloride or a mixture of crystalline form III and crystalline form V of 3-[2-(dimethylamino)methyl(cyclohex-1-yl)]phenol hydrochloride at a temperature between 150° C. and 160° C. until complete formation of crystalline form II occurs; or
 b) stirring crystalline form III of 3-[2-(dimethylamino)methyl(cyclohex-1-yl)]phenol hydrochloride and crystalline form III of 3-[2-(dimethylamino)-methyl-(cyclohex-1-yl)]phenol hydrochloride or crystalline form IV of 3-[2-(dimethylamino)methyl(cyclohex-1-yl)]phenol hydrochloride in a solvent until complete formation of crystalline form II occurs; or
 c) stirring a suspension of amorphous 3-[2-(dimethylamino)methyl(cyclohex-1-yl)]-phenol hydrochloride in a solvent as a carrier at a temperature between 30° C. and 50° C., until complete formation of crystalline form II occurs; or
 d) stirring crystalline form III of 3-[2-(dimethylamino)methyl(cyclohex-1-yl)]-phenol hydrochloride and crystalline form IV of 3-[2-(dimethylamino)methyl-(cyclohex-1-yl)]phenol hydrochloride in a solvent until complete formation of crystalline form II occurs.

6. A process according to claim 5, wherein:
 the heat treatment in a) is effected at a temperature between 154° C. and 158° C.; or
 the solvent in c) is a solvent that does not form solvates, and the stirring is effected at a temperature between 35° C. and 45° C.

7. A pharmaceutical composition comprising a crystalline salt of 3-[2-(dimethyl-amino)methyl(cyclohex-1-yl)]phenol hydrochloride according to claim 1 and at least one pharmaceutical carrier or diluent, wherein said salt is present as crystalline form II.

8. A method of treating pain in a subject in need thereof, said method comprising administering to said subject an analgesically effective amount of a crystalline salt according to claim 1.

9. A method of treating pain in a subject in need thereof, said method comprising administering to said subject an analgesically effective amount of a crystalline salt according to claim 3.

10. A method of treating pain in a subject in need thereof, said method comprising administering to said subject an analgesically effective amount of a crystalline salt according to claim 4.

* * * * *